(12) United States Patent
Miyakawa et al.

(10) Patent No.: US 9,506,070 B2
(45) Date of Patent: Nov. 29, 2016

(54) APTAMER AGAINST MIDKINE AND APPLICATIONS THEREOF

(71) Applicants: RIBOMIC INC., Tokyo (JP); OTSUKA PHARMACEUTICAL CO., LTD., Tokyo (JP)

(72) Inventors: Shin Miyakawa, Tokyo (JP); Masatoshi Fujiwara, Tokyo (JP); Yoshikazu Nakamura, Tokyo (JP); Kenji Kadomatsu, Aichi (JP); Ping Mu, Aichi (JP)

(73) Assignees: RIBOMIC INC., Tokyo (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/646,104

(22) PCT Filed: Nov. 21, 2013

(86) PCT No.: PCT/JP2013/081451
§ 371 (c)(1),
(2) Date: May 20, 2015

(87) PCT Pub. No.: WO2014/080997
PCT Pub. Date: May 30, 2014

(65) Prior Publication Data
US 2015/0353933 A1 Dec. 10, 2015

(30) Foreign Application Priority Data

Nov. 21, 2012 (JP) ................................. 2012-255588

(51) Int. Cl.
| | | |
|---|---|---|
| *C07H 21/02* | (2006.01) | |
| *C07H 21/04* | (2006.01) | |
| *C12N 15/115* | (2010.01) | |
| *A61K 47/48* | (2006.01) | |
| *A61K 31/7088* | (2006.01) | |
| *A61K 31/713* | (2006.01) | |
| *A61K 31/7105* | (2006.01) | |
| *A61K 31/711* | (2006.01) | |

(52) U.S. Cl.
CPC ......... *C12N 15/115* (2013.01); *A61K 31/7088* (2013.01); *A61K 31/711* (2013.01); *A61K 31/713* (2013.01); *A61K 31/7105* (2013.01); *A61K 47/48092* (2013.01); *C12N 2310/16* (2013.01); *C12N 2310/321* (2013.01); *C12N 2310/322* (2013.01); *C12N 2310/335* (2013.01); *C12N 2310/351* (2013.01); *C12N 2310/531* (2013.01); *C12N 2320/30* (2013.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 2010/0004432 A1 | 1/2010 | Miyakawa et al. |
| 2010/0092488 A1 | 4/2010 | Suzumura et al. |

FOREIGN PATENT DOCUMENTS

| | | |
|---|---|---|
| EP | 1 964 574 | 9/2008 |
| WO | 2007/055378 | 5/2007 |
| WO | 2008/059877 | 5/2008 |
| WO | 2009/063998 | 5/2009 |

OTHER PUBLICATIONS

Muramatsu (Current Pharmaceutical Design, 2011, 17, 410-423).*
Brody et al. (Reviews in Molecular Biotechnology, 74, 2000, 5-13).*
International Search Report dated Feb. 25, 2014 issued in International PCT Application No. PCT/JP2013/081451.
J. Wang, et al., "Inhibition of midkine alleviates experimental autoimmune encephalomyelitis through the expansion of regulatory T cell population", Proc. Natl. Sci., USA, Mar. 2008, vol. 105, No. 10, pp. 3915-3920.

(Continued)

*Primary Examiner* — Amy Bowman
(74) *Attorney, Agent, or Firm* — Wenderoth, Lind & Ponack, L.L.P.

(57) ABSTRACT

The present invention provides an aptamer binding to midkine and capable of forming a potential secondary structure represented by the formula (I):

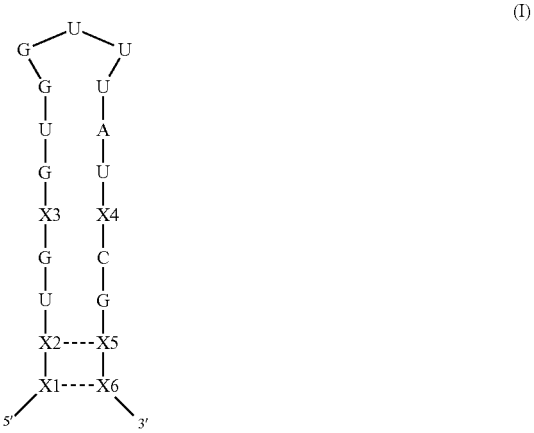

wherein
X1, X2, X5 and X6 are the same or different and each is one or two nucleotides selected from the group consisting of A, G, C, U and T, or a bond,
X1 and X6, and X2 and X5 each form a Watson-Crick base pairs, and
X3 and X4 are the same or different and each is a nucleotide selected from A, G, C, U and T.

17 Claims, 5 Drawing Sheets

(56) References Cited

OTHER PUBLICATIONS

Y. Sonobe, et al., "Midkine Inhibits Inducible Regulatory T Cell Differentiation by Suppressing the Development of Tolerogenic Dendritic Cells", J. Immunol., Feb. 2012, vol. 188, pp. 2602-2611.

Y. Nakamura, et al., "RNA plasticity and selectivity applicable to therapeutics and novel biosensor development", Genes to Cells, May 2012, vol. 17, pp. 344-364.

Y. Takei, et al., "Combinational Antitumor Effect of siRNA Against Midkine and Paclitaxel on Growth of Human Prostrate Cancer Xenografts", Cancer, 2006, vol. 107, pp. 864-876.

S. Kishida, et al., "Midkine Promotes Neuroblastoma through Notch2 Signaling", Cancer Res., 2012, vol. 73, No. 4, pp. 1318-1327.

H. Maehara, et al., "Midkine as a novel target for antibody therapy in osteosarcoma", Biochem. Biophys. Res. Commun., 2007, vol. 358, pp. 757-762.

L.C. Dai, et al., "Antisense oligonucleotides targeting midkine inhibit tumor growth in an in situ human hepatocellular carcinoma model", Acta Pharmacol Sin., 2007, vol. 28, No. 3, pp. 453-458.

Takashi Muramatsu, "Midkine and Pleiotrophin: Two Related Proteins Involved in Development, Survival, Inflammation and Tumorigenesis", J. Biochem, Nov. 3, 2002, vol. 132, No. 3, pp. 359-371.

* cited by examiner

APTAMER AGAINST MIDKINE AND APPLICATIONS THEREOF

TECHNICAL FIELD

The present invention relates to an aptamer against midkine and use thereof.

BACKGROUND ART

Midkine (hereinafter sometimes abbreviated as "MK" as required) is a growth/differentiation factor that was first discovered as a gene product expressed transiently in the process of differentiation induction of embryonic tumor cells (EC) with retinoic acid, being a polypeptide having a molecular weight of 13 kDa, rich in basic amino acids and cysteine.

The steric structure of MK has been determined by NMR and reported. When characterized structurally, MK is configured mainly with two domains. Specifically, MK consists of a fragment on the N-terminal side consisting of amino acid residues 1 to 52 (hereinafter referred to as "the N-fragment"), a fragment on the C-terminal side consisting of amino acid residues 62 to 121 (hereinafter referred to as "the C-fragment") and a loop region that connects the fragments (amino acid residues 53 to 61). In the MK molecule, each of the N-fragment and the C-fragment has a steric structure consisting mainly of three reversed β sheet structures (hereinafter referred to as "domains"; a domain consisting of the amino acid residues 15 to 52 in the N-fragment referred to as "the N-domain", a domain consisting of the amino acid residue 62 to 104 in the C-fragment referred to as "the C-domain"), and freely moving structures assuming no particular structure (hereinafter referred to as "tails"; a tail consisting of the amino acid residues 1 to 14 in the N-fragment referred to as "the N-tail", and a tail consisting of the amino acid residues 105-121 in the C-fragment referred to as "the C-tail"). Bound to the outside of each domain is a tail that is rich in basic amino acids.

Known receptors of MK include receptor-type protein tyrosine phosphatase ζ (PTPζ), LRP (low density lipoprotein receptor-related protein), ALK (anaplastic leukemia kinase), integrin and syndecan and the like. MK is a highly positively charged protein containing large amounts of the basic amino acids lysine (K) and arginine (R). It has a heparin-binding site in the C-domain thereof, and is known to bind strongly to negatively charged molecules such as heparin and chondroitin sulfate E.

MK is a protein important in the developmental process, and is strongly expressed in midembryo. In contrast, expression in adults is limitative, and MK expression is found in vascular endothelium and particular mucosal epithelium. When a tissue is damaged, MK expression at the site increases, or newly induced. The produced MK promotes survival and movement of cells, and further exhibits various biological activities such as cell proliferation, altered morphology, chemokine expression and the like.

MK is also related to cancer, and MK expression is known to increase in many of human cancers. Such phenomenon has been observed in a wide variety of cancers, including esophageal cancer, thyroid cancer, urinary bladder cancer, colorectal cancer, gastric cancer, pancreatic cancer, thoracic cancer, liver cancer, lung cancer, breast cancer, neuroblastoma, glioblastoma, uterine cancer, ovarian cancer, prostate cancer and Wilms' tumor. By comparison of each case of various carcinomas, MK expression increases in about 80% of the cases. It has been reported an increase in the expression of MK was found in all cases of Wilms' tumor developed by the deletion of WT1 cancer suppressive gene and tumor in the nerve system caused by the deletion of NF-1 cancer suppressive gene.

MK with increased expression is also considered to promote the survival and movement of cancer cells and facilitate neovascularization to help the advancement of cancer. In neuroblastoma, urinary bladder cancer, glioblastoma and the like, it is known that prognosis is poorer in cancer patients with high MK expression than cancer patients with low MK expression. In a cell line derived from human gastric cancer, there is a strong correlation between resistance to anti-cancer agent and high expression of MK. In the cells derived from human liver cancer, MK is deeply involved in the cell proliferation thereof, and is also known to inhibit apoptosis of the cells.

From such relationship between MK and cancer, simultaneously with the utilization of MK to tumor marker, the development of a therapeutic drug for cancer targeting MK is attracting attention. As a therapeutic drug for cancer, one suppressing an increase in the expression of MK is designed, and antibody, siRNA, antisense oligoDNA and the like to MK have been studied (non-patent documents 1-3).

In recent years, applications of RNA aptamers to medicaments, diagnostic agents, and test drugs have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target substance such as a protein, and can be prepared using the SELEX (Systematic Evolution of Ligands by Exponential Enrichment) method. In the SELEX, an RNA that binds specifically to a target substance is selected from an RNA pool with about $10^{14}$ different nucleotide sequences. The RNA structure used has a random sequence of about 40 residues, which is flanked by primer sequences. This RNA pool is allowed to be assembled with a target substance, and only the RNA that has bound to the target substance is collected using a filter and the like. The RNA collected is amplified by RT-PCR, and this is used as a template for the next round. By repeating this operation about 10 times, an RNA aptamer that binds specifically to the target substance can be acquired. There are already some reports on the aptamer for MK (patent documents 1-3, non-patent document 4).

Aptamer drugs, like antibody drugs, can target extracellular factors. With reference to many scientific papers and other reference materials in the public domain, aptamer drugs are judged to potentially surpass antibody drugs in some aspects. For example, aptamers often show higher binding force and higher specificity than do antibodies. Aptamers are unlikely to undergo immune elimination, and adverse reactions characteristic of antibodies, such as antibody-dependent cell-mediated cytotoxicity (ADCC) and complement-dependent cytotoxicity (CDC), do not occur with the use of aptamers. From the aspect of delivery, since aptamers are about 1/10 of antibody in size, delivery of a drug to the object site is easier. Since aptamers are produced by chemical synthesis, various modifications can be made easily, reduction of cost by large-scale production is possible. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

DOCUMENT LIST

Patent Documents patent document 1: WO 2007/055378
patent document 2: WO 2008/059877
patent document 3: WO 2009/063998

Non-Patent Documents non-patent document 1: Maehara, H. et al., (2007) Biochem. Biophys. Res. Commun. 358: p. 757-762
non-patent document 2: Takei, Y. et al., (2006) Cancer. 107: p. 864-873
non-patent document 3: Dai, L. C. et al., (2007) Acta Pharmacol. Sin. 28: p. 453-458
non-patent document 4: Wang, J. et al., (2008) Proc. Natl. Acad. Sci., USA 105: p. 3915-3920

SUMMARY OF THE INVENTION

Problems to be Solved by the Invention

The present invention aims to provide an aptamer against midkine and a utilization method thereof and the like. Particularly, it aims to provide an aptamer suitable for use as a pharmaceutical product such as a therapeutic drug for cancer and the like, and further, an aptamer having a midkine activity (cancer cell binding activity) inhibitory action even with a short chain length, and high specificity for midkine.

Means of Solving the Problems

The present inventors investigated diligently to solve the problem described above, and, as a result, succeeded in producing a novel aptamer having a remarkably high inhibitory effect on the cancer cell binding activity of midkine, which resulted in the completion of the present invention.

Accordingly, the present invention relates to the following.

[1] An aptamer binding to midkine and capable of forming a potential secondary structure represented by the formula (I):

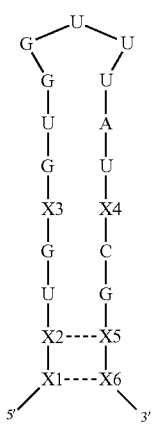

(I)

wherein
X1, X2, X5 and X6 are the same or different and each is one or two nucleotides selected from the group consisting of A, G, C, U and T, or a bond,
X1 and X6, and X2 and X5 each form a Watson-Crick base pairs, and
X3 and X4 are the same or different and each is a nucleotide selected from A, G, C, U and T.
[2] The aptamer of [1], wherein X1, X2, X5 and X6 are the same or different and each is one nucleotide selected from the group consisting of A, G, C, U and T.
[3] The aptamer of [1] or [2], wherein X3 is A or U, and X4 is C.
[4] A nucleic acid having a length of 15 to 100 nucleotides and comprising a nucleic acid of any of the following (a)-(c) partly or entirely:
(a) a nucleic acid defined as any of SEQ ID NOs: 1-12 and 20;
(b) the nucleic acid of the above-mentioned (a), wherein one to several nucleotides are substituted, deleted, inserted or added, which binds to midkine;
(c) the nucleic acid of the above-mentioned (a) or (b), wherein a group at the 2'-position of ribose of one or plural nucleotides is substituted by other group.
[5] The aptamer or nucleic acid of any of [1]-[4], which has a nucleotide length of not more than 45.
[6] The aptamer or nucleic acid of any of [1]-[5], wherein at least one nucleotide is modified.
[7] The aptamer or nucleic acid of [5] or [6], which is modified with inverted dT or polyethylene glycol.
[8] The aptamer or nucleic acid of [7], wherein inverted dT or polyethylene glycol is bonded to the 5'-terminus or 3'-terminus of the aptamer or nucleic acid.
[9] The aptamer or nucleic acid of any of [5]-[8], wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group.
[10] The aptamer or nucleic acid of any of [5]-[8], wherein the hydroxyl groups at the 2'-position of a ribose of respective purine nucleotides are the same or different and unreplaced or replaced by an atom or group selected from the group consisting of a hydrogen atom, a fluorine atom and a methoxy group.
[11] The aptamer or nucleic acid of any of [1]-[10], which inhibits midkine from binding to a cancer cell.
[12] The aptamer or nucleic acid of any of [1]-[10], which inhibits midkine-dependent cell proliferation.
[13] A pharmaceutical composition comprising the aptamer or nucleic acid of any of [1]-[12].
[14] A therapeutic drug for cancer comprising the aptamer or nucleic acid of any of [1]-[12]

Effect of the Invention

The aptamer or nucleic acid of the present invention having the above-mentioned constitution shows a superior MK activity inhibitory action, particularly a superior action in the inhibition of the binding activity of MK to a cancer cell, it can be useful as a therapeutic drug for cancer.

DESCRIPTION OF EMBODIMENTS

Figure 1:
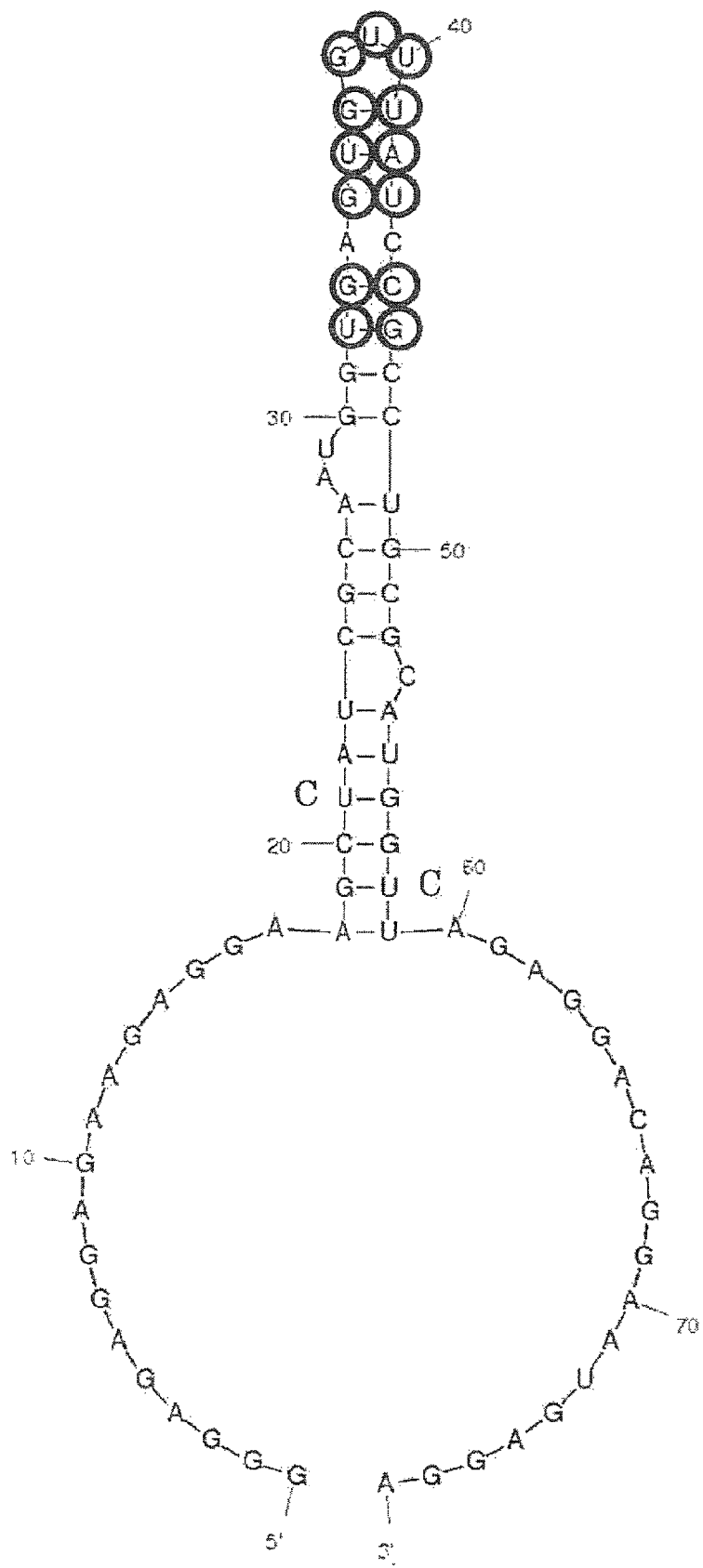
FIG. 1 shows a secondary structure prediction of the oligonucleotide shown in SEQ ID NO: 1.

The present invention provides an aptamer binding to midkine and capable of forming a potential secondary structure represented by the formula (I):

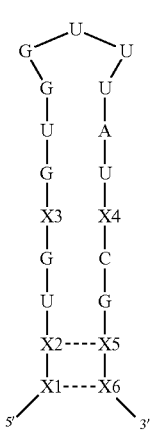

wherein
X1, X2, X5 and X6 are the same or different and each is one or two nucleotides selected from the group consisting of A, G, C, U and T, or a bond,
X1 and X6, and X2 and X5 each form a Watson-Crick base pairs, and
X3 and X4 are the same or different and each is a nucleotide selected from A, G, C, U and T (hereinafter sometimes to be referred to as "the aptamer of the present invention").

An aptamer refers to a nucleic acid molecule having a binding activity for a particular target molecule. The aptamer can inhibit the activity of a particular target molecule by binding to the particular target molecule. The aptamer of the present invention is an aptamer having a binding activity to MK. According to preferable embodiment, the aptamer of the present invention can inhibit the activity of MK by binding to MK and inhibiting the binding of MK and MK receptor.

The aptamer of the present invention can be a nucleic acid such as an RNA, a DNA, a modified nucleic acid or a mixture thereof. Accordingly, the aptamer of the present invention may be indicated as "the nucleic acid of the present invention" in the following.

The single-stranded nucleic acid can have various secondary structures. The "potential secondary structure" means a secondary structure that a certain single-stranded nucleic acid can take thermodynamically in view of its primary structure. Particularly, the potential secondary structure of the aptamer of the present invention is a secondary structure predictable using the MFOLD program described in Example 1 mentioned below. Accordingly, even a nucleic acid not currently having a secondary structure represented by the above-mentioned formula (I) is encompassed in the aptamer of the present invention, as long as it has a primary structure capable of forming said secondary structure.

Preferably, therefore, the aptamer of the present invention is a nucleic acid molecule wherein the consensus sequence (X1) (X2)UG(X3)GUGGUUUAU(X4)CG(X5) (X6) (SEQ ID NO: 20) can have a secondary structure represented by the above-mentioned formula (I) thermodynamically stably in view of the primary structure thereof.

The potential secondary structure represented by the formula (I) is what is called a "stem-loop structure", characteristically having, particularly, a stem structure that can be formed by a combination of X1-X2-U-G-X3-G-U-G and U-A-U-X4-C-G-X5-X6, and a loop structure, which links the both nucleotide sequences, between the terminal bases G and U of the nucleotide sequences.

The "stem structure" is a structure wherein partial nucleotide sequences having complementarity in a nucleic acid molecule form Watson-Crick base pairs (G-C or A-U/T). In the present Description, the above-mentioned both nucleotide sequences do not need to be completely complementary, and mismatch and/or wobbling of G-U/T are/is permitted. That is, as long as the nucleotides on a partial nucleotide sequence forming a stem structure form Watson-Crick base pairs, all other nucleotides are not necessarily required to form Watson-Crick base pairs.

In the formula (I), X1, X2, X5 and X6 are the same or different and each is a bond or 1 or 2 nucleotides selected from the group consisting of A, G, C, U and T. When Xi (i is an integer selected from 1, 2, 5 and 6) shows "two nucleotides", said two nucleotides may be the same or different. When Xi shows "two nucleotides" or "a bond", it is preferably contained in each partial sequence of X1-X2 and X5-X6 in the number of not more than 1. The above-mentioned "bond" means a single bond, and when any Xi in the formula (I) is "a bond", it means that the nucleotides adjacent to the nucleotide are linked to each other via a phosphodiester bond.

Particularly preferably, X1, X2, X5 and X6 are the same or different and each is one nucleotide selected from the group consisting of A, G, C, U and T.

X1 and X6, and X2 and X5, each form Watson-Crick base pairs (G-C or A-U/T, or the inverse thereof). When X1 or X2 is a bond, X6 or X5 is also a bond. A base pair consisting of X2 and X5 is preferably in the relationship of G-C or C-G. The stem structure preferably forms a base pair of at least 2 bases in the terminal region on the side opposite to the loop structure. This stem structure is important for forming the above-mentioned structure of the formula (I) and, in the aptamer of the present invention, the structure is not limited to the above-mentioned formula (I) part and preferably has a still longer stem length by forming Watson-Crick base pairs of nucleotide sequences that bind to the both ends thereof (mismatch and/or wobbling of G-U/T are/is allowed).

In the formula (I), X3 and X4 are the same or different and each is a nucleotide selected from A, G, C, U and T. X3 and X4 may or may not form Watson-Crick base pairs. X3 is preferably A or U, and X4 is preferably C.

Alternatively, the aptamer of the present invention may be an aptamer binding to midkine and capable of forming a potential secondary structure represented by the formula (I'), which is the same as the above-mentioned formula (I) except that the stem structure is extended by one more base pair:

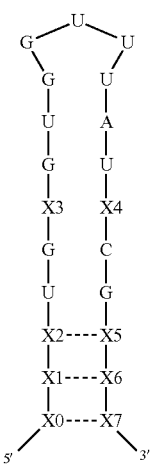

(I')

wherein X1-X6 are as mentioned above, and X0 and X7 are nucleotides forming Watson-Crick base pairs. In this case, while X0 and X7 are not particularly limited as long as Watson-Crick base pairs are formed, they are preferably in the relationship of G-C or C-G.

The present invention also provides a nucleic acid having a length of 15 to 100 nucleotides and comprising a nucleic acid of any of the following (a)-(c) partly or entirely:
(a) a nucleic acid defined as any of SEQ ID NOs: 1-12 and 20;
(b) the nucleic acid of the above-mentioned (a), wherein one to several nucleotides are substituted, deleted, inserted or added, which binds to midkine;
(c) the nucleic acid of the above-mentioned (a) or (b), wherein a group at the 2'-position of ribose of one or plural nucleotides is substituted by other group.

Such nucleic acids can form a potential secondary structure represented by the above-mentioned formula (I).

While any uracil on any sequence can be replaced by thymine, the uracil to be replaced can be preferably one in a part other than the loop structure in the aforementioned potential secondary structure, so that the activity of the aptamer of the present invention can be maintained.

In the present Description, a sequence specified by "SEQ ID NO" means a nucleotide sequence of each aptamer or nucleic acid and, for example, "a nucleic acid comprising the nucleotide sequence shown by SEQ ID NO: 1" means a natural nucleic acid or modified nucleic acid comprising the nucleotide sequence shown by SEQ ID NO: 1 or a nucleic acid constituted with the both. The "nucleic acid defined as SEQ ID NO: 1" means a nucleic acid having a particular modification at the 2'-position of ribose as described in the below-mentioned Examples, wherein modification of other sugar moiety or dinucleotide bond is optional. The nucleic acid defined as SEQ ID NO: 20 means any nucleic acid consisting of the nucleotide sequence shown in SEQ ID NO: 20, and contained as a part of the nucleic acid defined as SEQ ID NO: 1-12. The base sequence of SEQ ID NO of each aptamer is described in the Sequence Listing attached to the specification.

In the above-mentioned (b), the number of the nucleotides substituted, deleted, inserted or added is, for example, 1-5, further preferably 1-3, most preferably 1 or 2.

In the above-mentioned (b), while the position of the nucleotide to be substituted, deleted, inserted or added is not particularly limited, the nucleotide can be preferably in a part other than the loop structure in the aforementioned potential secondary structure, so that the activity of the aptamer of the present invention can be maintained. Alternatively, the positions of the nucleotides to be substituted, deleted, inserted or added may be other than the consensus sequence: UGXGUGGUUUAUCCG (X=A or U; SEQ ID NO: 21) commonly contained in SEQ ID NOs: 1-12 and 20.

In the above-mentioned (c), while other group used for substituting the 2'-position of ribose of one or plural nucleotides is not particularly limited, to maintain or improve the activity that the aptamer of the present invention has, it is preferably a group selected from the group consisting of a hydroxyl group, a hydrogen atom, a fluorine atom and an —O-Me group. The number of nucleotides wherein the group at the 2'-position of ribose is substituted by other group may be, for example, 1-20, preferably 1-15, more preferably 1-10, further preferably 1-5. The number of modified nucleotides in the consensus sequence: UGXGUG-GUUUAUCCG (X=A or U; SEQ ID NO: 21) common to SEQ ID NOs: 1-12 and 20 is desirably 1-5.

While the nucleotide length of the aptamer or nucleic acid of the present invention is not particularly limited, it is generally 15-about 100 nucleotides, preferably 15-about 80 nucleotides, more preferably 18-60 nucleotides, further preferably 20-45 nucleotides. The chemical syntheses and mass-production of the aptamer become easier by reducing the total number of nucleotides to fall within the range permitting formation of the potential secondary structure represented by above-mentioned formula (I), and there is a major advantage in terms of cost. Such aptamer is also considered to permit easy chemical modification, high stability in the body, and low toxicity.

The aptamer of the present invention may also be a conjugate selected from the group consisting of a conjugate of a plurality of nucleic acids of the above-mentioned (a), a conjugate of a plurality of nucleic acids of the above-mentioned (b), a plurality of nucleic acids of the above-mentioned (c), and a conjugate of a plurality of two more kinds of nucleic acids selected from the nucleic acid of the above-mentioned (a), the nucleic acid of the above-mentioned (b) and the nucleic acid of the above-mentioned (c).

These conjugates can also bind to MK and/or inhibit the activity of MK (MK receptor binding activity etc.).

Conjugation herein can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4.

In the aptamer and nucleic acid of the present invention, one or several, for example, 1-2, 1-3, 1-4, 1-5 nucleotides may be substituted by Bridged Nucleic Acid (BNA) to stabilize aptamer and improve the activity thereof. As used herein, the "bridged nucleic acid" refers to one having a structure wherein the binding affinity to a complementary sequence is enhanced by restricting the degree of freedom of nucleic acid by intramolecular crosslinking to acquire nuclease resistance. Examples thereof include, but are not limited to, 2',4'-BNA (Locked Nucleic Acid (LNA)), 2'-O,4'-C- ethylene-bridged Nucleic Acid (ENA) and the like. In the aptamer and nucleic acid of the present invention, a part of or whole chemical structure of a phosphoric acid diester bond of the nucleotide may be modified or substituted by any substituent. For example, phosphoric acid diester bond may be substituted by a phosphorothioate bond, a phosphorodithioate bond, an alkylphosphonate bond, a phosphoramidate bond and the like.

Each nucleotide contained in the aptamer of the present invention is the same or different and can be a nucleotide comprising a hydroxyl group at the 2'-position of ribose (e.g., ribose of pyrimidine nucleotide, ribose of purine nucleotide) (i.e., unsubstituted nucleotide) or a nucleotide wherein a hydroxyl group is replaced by any atom or group at the 2'-position of ribose.

As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH$_2$ group) can be mentioned. In the following cases, the hydroxyl group is replaced by a hydrogen atom, a fluorine atom or —O-Me group, respectively, at the 2'-position of ribose.

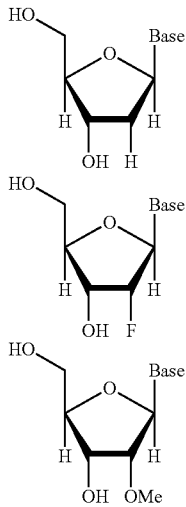

The aptamer of the present invention can also be the nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2'-position of ribose.

Also, in the aptamer of the present invention, all pyrimidine nucleotides may be nucleotides wherein the 2'-position of ribose is substituted by a fluorine atom, or may be the same or different nucleotides wherein a fluorine atom is substituted by any atom or group mentioned above, preferably an atom or group selected from the group consisting of a hydrogen atom, a hydroxyl group and a methoxy group at the 2'-position of ribose. Particularly, when a production method using the below-mentioned DuraScribe™ T7 Transcription Kit (manufactured by Epicentre) is applied as a production method of the aptamer of the present invention, an aptamer wherein the hydroxyl group at the 2'-position of ribose of all pyrimidine nucleotides is fluorinated is obtained. The aptamer of the present invention substituted by other above-mentioned atom or group can be produced by the below-mentioned method.

In the aptamers of the present invention, moreover, all purine nucleotides may be nucleotides wherein a hydroxyl group is not substituted at the 2'-position of ribose, or the same or different nucleotides wherein a hydroxyl group is substituted by any atom or group mentioned above, preferably an atom or group selected from the group consisting of a hydrogen atom, a methoxy group and a fluorine atom at the 2'-position of ribose. These aptamers of the present invention can be produced by the below-mentioned method.

In this Description, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, replacement of the hydroxyl group at the 2'-position of ribose by X should read as a replacement of one hydrogen atom at the 2'-position of deoxyribose by X.

When uracil is substituted with thymine in the aptamer of the present invention, MK-binding activity, MK-MK receptor binding inhibitory activity, MK cancer cell binding activity, stability, drug deliverability and stability in blood of the aptamer and the like can be increased.

MK to which the aptamer of the present invention binds is a known protein rich in basic amino acid and cysteine, which is a secreted protein playing an important role in the preservation and repair of injured tissues. The amino acid sequence of human MK is shown by GenBank accession number BC011704, the secretory protein being configured with 121 amino acid residues from lysine 23 to aspartic acid 143. Generally, the lysine residue 23 is denoted by the amino acid residue at position 1. Human MK consists of an N-fragment consisting of amino acid residues 1 to 52, a C-fragment consisting amino acid residues 62 to 121 and a loop region that connects the fragments, but the boundary of the N-fragment and the C-fragment may be any loop portion of MK (53-61), and cannot be defined precisely. MK in the present invention may be the above-mentioned protein with mutation, its functional domain or peptide fragment. It may be not only a monomer but also a dimer or multimer. Furthermore, it includes MK derived from non-human mammals, for example, primates (e.g., monkey), rodents (e.g., mouse, rat, guinea pig), and companion animals, domestic animals and working animals (e.g., dog, cat, horse, bovine, goat, sheep, swine).

The aptamer of the present invention is not particularly limited as long as it can bind to any part of MK and inhibit its activity. For example, it can bind to N-fragment, C-fragment or both of MK and inhibit the activity of MK.

In the present Description, the "MK activity inhibitory action" means an inhibitory ability on any activity MK has. For example, it means an activity to inhibit MK from binding to MK receptor, inhibition of signal transduction in the downstream of MK receptor (PI3 kinase pathway, MAP kinase pathway), inhibition of biological activity of MK (growth, survival, altered morphology and movement of cells, chemokine expression, angiogenesis etc.), further, inhibition of binding activity of MK to cancer cells, suppression of migration of inflammatory cells, suppression of growth of endometrium interstitial cells, inhibition of vascular intimal thickening activity and the like. A preferable "MK activity inhibitory action" of the aptamer of the present invention includes inhibition of binding activity of MK to cancer cells and the like.

The aptamer of the present invention binds to MK in a physiological buffer (e.g., solution A: see Example 1). The aptamer of the present invention binds to, for example, MK at an intensity detectable by the following test.

For the measurement, BIAcore2000 manufactured by BIAcore is used. An aptamer is immobilized on a sensor chip. The amount to be immobilized is set to 1000 RU. A physiological buffer (solution A: see Example 1) is used to prepare MK solution (0.5 μM). This MK solution (70 μL) is injected and the binding of MK to the aptamer is detected. When a binding signal is observed from the obtained wave form data, the aptamer is determined to have a binding capacity to MK.

In the present specification, the "MK receptor" means a cell surface protein that MK binds to. Known receptors of MK include receptor-type protein tyrosine phosphatase ζ (PTPζ), LRP (low density lipoprotein receptor-related protein), ALK (anaplastic leukemia kinase), integrin and syndecan and the like. The MK receptor referred to in the present invention may be a protein containing a natural amino acid sequence or a variant thereof. Here, the "variant thereof" means a protein or peptide wherein several amino acids of an amino acid sequence of "MK receptor" have been substituted, or a partial amino acid sequence thereof, which has a binding activity to MK. In the present invention, MK receptor is preferably a protein on the surface of a cancer cell.

The aptamer of the present invention can inhibit the binding activity of MK to a cancer cell. Whether the aptamer of the present invention inhibits the binding activity of MK to a cancer cell can be evaluated by, for example, the test described in Example 5.

In the aptamer of the present invention, a sugar residue (e.g., ribose) of each nucleotide may be modified to enhance bindability to MK, MK and MK receptor binding-inhibitory activity, cancer cell binding activity of MK, stability of aptamer, drug deliverability, stability in blood and the like. Examples of the modification in a sugar residue include replacement of the oxygen atom at the 2'-position, 3'-position and/or 4'-position of the sugar residue with other atom, and the like, particularly, replacement of the hydroxyl group at the ribose 2'-position with other atom. As the kind of the modification, fluorination, O-alkylation (e.g., O-methylation, O-ethylation), O-arylation, S-alkylation (e.g., S-methylation, S-ethylation), S-arylation, and amination (e.g., $-NH_2$) can be mentioned. In addition, examples thereof include 4'-SRNA wherein the 4'-position oxygen is replaced with sulfur, LNA (Locked Nucleic Acid) wherein the 2'-position and the 4'-position are crosslinked via methylene, 3'-N-phosphoramidate nucleic acid wherein the 3'-position hydroxyl group is replaced with an amino group and the like. The aptamer of the present invention is sometimes produced with a given modification of the oxygen atom at the 2'-position of ribose of pyrimidine nucleotide, due to the production method thereof. When a production method using the below-mentioned DuraScribe™ T7 Transcription Kit (manufactured by Epicentre) is applied as a production method of the aptamer of the present invention, an aptamer wherein the hydroxyl group at the 2'-position of ribose of preferably all pyrimidine nucleotides is fluorinated is produced. Therefore, it is possible to produce various variations of aptamers having enhanced activity even though the base sequence is the same, by applying such alteration in the sugar residue to the obtained aptamer. From the above, the aptamer of the present invention can be preferably an aptamer wherein a sugar residue of at least one nucleotide is modified. Such alterations in the sugar residue can be performed by a method known per se (see, for example, Sproat et al., (1991) Nucle. Acid. Res. 19, 733-738; Cotton et al., (1991) Nucl. Acid. Res. 19, 2629-2635; Hobbs et al., (1973) Biochemistry 12, 5138-5145). To be specific, an aptamer wherein the hydroxyl group at the 2'-position of ribose is substituted by an atom or group selected from the group consisting of a hydrogen atom, a hydroxyl group and a methoxy group can be produced by using, as a base, an aptamer wherein the hydroxyl group at the 2'-position of ribose of all pyrimidine nucleotides is substituted by a fluoro group.

The aptamer of the present invention may be one wherein a sugar residue of at least one nucleotide is modified, as shown in the below-mentioned Examples. Particularly, of the aptamers of the present invention, aptamers of the formula (I)

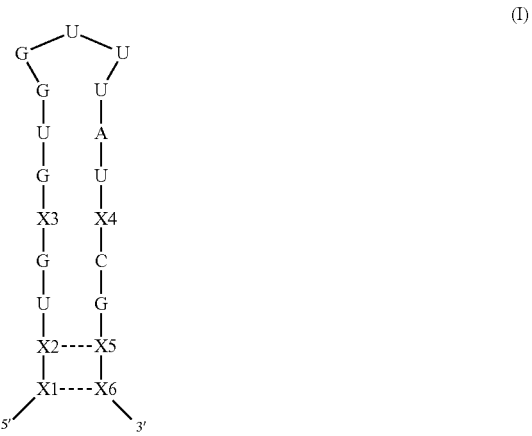

wherein X1-X6 are as defined above,
the formula (I')

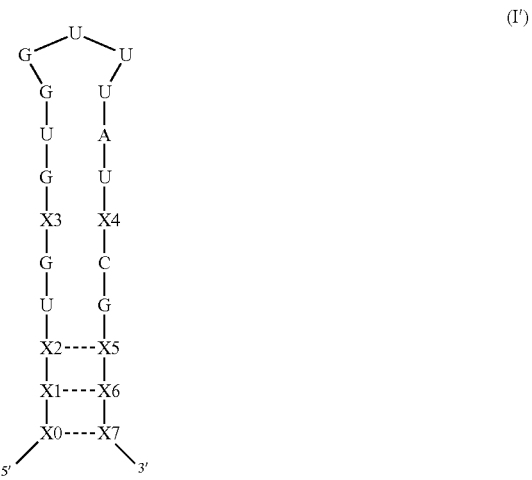

wherein X0-X7 are as defined above, and
the consensus sequence of the aptamer of the present invention, which is contained in each of the above-mentioned formulas, (SEQ. ID. NO: 20)
(X1) (X2) UG (X3) GUGGUUCAU (X4) CG (X5) (X6), in each of which formulas the hydroxyl group at the ribose 2'-position of the 2nd U from the 5'-side (excluding X1-X3; shown with thick underline) is fluorinated, are desirable for maintaining the activity. Also, it is sometimes preferable for improving the activity that the hydroxyl group at the ribose 2'-position of the 3rd, 4th and 5th G from the 5'-side (excluding X1-X4; enclosed with circle) in the consensus sequence be methoxylated and, in addition thereto, the hydroxyl group at the ribose 2'-position of the 2nd U from the 3'-side (excluding X4-X6; enclosed with circle) be further methoxylated. On the other hand, it is sometimes preferable for improving the activity that the hydroxyl group at the ribose 2'-position of the 1st G and/or A from the 5'-side (excluding X1-X3; enclosed with square) in the consensus sequence be not methoxylated.

The aptamer of the present invention may also have a nucleic acid base (e.g., purine or pyrimidine) altered (e.g., chemical substitution) to increase the MK-binding activity, MK-MK receptor binding inhibitory activity, MK cancer cell binding activity, stability, drug deliverability, and stability in blood of the aptamer and the like. As examples of such alterations, pyrimidine alteration at 5-position, purine alteration at 6- and/or 8-position(s) (O-methyl modification and the like), alteration with an extracyclic amine, substitution with 4-thiouridine, substitution with 5-bromo or 5-iodo-uracil, modification of 5-amino acid type and modification of 5-tryptophan side chain can be mentioned. The phosphate group contained in the aptamer of the present invention may be altered to confer resistance to nuclease and hydrolysis. For example, the phosphate region of the aptamer may be replaced with P(O)S (thioate), P(S)S (dithioate), P(O)NR$_2$ (amidate), P(O)R, P(O)OR', CO or CH$_2$ (formacetal), P(O)BH$_3$ (boranophosphate) or 3'-amine (—NH—CH$_2$—CH$_2$—) [wherein each unit of R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethyleneglycol (hereinafter, sometimes to be described as "PEG"), amino acid, peptide, inverted dT, myristoyl, lithocolic-oleyl, docosanyl, lauroyl, stearoyl, palmitoyl, oleoyl, linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

Particularly, when alteration is performed by terminus addition of PEG, the molecular weight of PEG is not particularly limited, and is preferably 1000-100000, more preferably 30000-90000. PEG may be linear or branched into two or more chains (multi-arm PEG).

Such PEG is not particularly limited, and those of ordinary skill in the art can appropriately select and use commercially available or known PEG (e.g., http://www.peg-drug.com/peg_product/branched.html). Specific preferable examples of the PEG to be applied to the aptamer of the present invention include 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION) and the like.

In this case, in the aptamer of the present invention, PEG may be directly added to the terminus' It is more preferable that a linker having a group bindable to PEG and the like be added to the terminus thereof, and PEG be added to the aptamer of the present invention via the linker.

The linker for PEG and the aptamer of the present invention is not particularly limited, and carbon chain number, functional group and the like can be appropriately selected according to the binding site, the kind of PEG and the like. Examples of such linker include a linker having an amino group. Specifically, when added to the 5' end, ssH Linker (SAFC) or DMS(O)MT-AMINO-MODIFIER (GLEN RESEARCH) can be mentioned, and when added to the 3' end, TFA Amino C-6 Icaa CPG (ChemGenes) and the like can be mentioned. When this linker is selected, for example, an active group of N-hydroxysuccinimide is added to PEG, and reacted with an amino group on the linker side, whereby the aptamer of the present invention can be bound to PEG via the linker.

As PEG and linker, commercially available products can be preferably used. The reaction conditions and the like relating to the binding of PEG, a linker and the aptamer of the present invention can be appropriately determined by those of ordinary skill in the art.

The aptamer of the present invention can be chemically synthesized as disclosed herein and by a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to the positive charge of lysine and arginine present on the surface of protein. For this reason, nucleic acid bases not involved in the direct binding to the target substance can be substituted. In particular, because the section of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to an active site of the target substance. Therefore, the aptamers obtained by SELEX do not necessarily act on the function of the target substance. MK has a lysine-rich region in the tail region of each of the N end and C end thereof, to which a nucleic acid is thought to bind nonspecifically. This tail portion is not considered to be important in the binding of heparin or chondroitin sulfate. It is not easy to prepare an aptamer that effectively inhibits an activity of MK in such an environment.

Based on an active aptamer thus selected, SELEX can be performed based on the sequence of the obtained aptamer to acquire an aptamer possessing higher activity. Specifically, after preparing a template wherein an aptamer with a determined sequence is partially randomized or a template doped with about 10 to 30% of random sequences, SELEX is performed again.

An aptamer obtained by SELEX has a length of about 80 nucleotides, and this is difficult to prepare as a medicament as it is. Hence, it is necessary to repeat try-and-error efforts to shorten the aptamer to a length of about 60 nucleotides or less enabling easy chemical synthesis, more preferably about 50 nucleotides or less, most preferably 45 nucleotides or less. Depending on the primer design for an aptamer obtained by SELEX, the ease of the subsequent minimization operation changes. Unless the primer is designed successfully, subsequent development will be impossible even if an aptamer with activity is selected by SELEX.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the obtained aptamer with the target substance is identified by repeated try-and-error efforts as described above, the activity remains unchanged in many cases even when a new sequence is added to both ends of the sequence. Such length of the new sequence is not particularly limited.

Modifications, like sequences, afford a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem section, internal loop section, hairpin loop section and single-strand section: hereinafter, abbreviated as fixed sequence as required).

For example, the production method of such aptamer includes production of an aptamer comprising a fixed sequence by using a single kind of nucleic acid molecule consisting of a nucleotide sequence shown by:

Primer sequence (i)-(N)a-fixed sequence-(N)b-Primer sequence (ii)

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The aptamer of the present invention is preferably an aptamer that binds to MK, characteristically contains the sequence shown by SEQ ID NO: 7-12, and has a nucleotide length of not more than 45.

The sequence shown by SEQ ID NO: 7-12 is a region important for the aptamer of the present invention to function as the aptamer of the present invention such as binding to MK and inhibiting the activity of MK, particularly binding activity to cancer cell and the like. Even when a new sequence is added to both ends of the sequence, the function of the aptamer of the present invention is not impaired. The sequence may be subject to modification of the aforementioned sugar residue, alteration of nucleic acid base and phosphate group, and the like.

Thus, preferable specific examples of the aptamer of the present invention include
aptamers comprising the sequence shown by SEQ ID NO: 7-12, having a nucleotide length of not more than 45, and binding to MK, which are
(i) an aptamer comprising at least one kind of nucleotide wherein the hydroxyl group is replaced by a hydrogen atom, a fluorine atom, a —O-alkyl group, a —O-acyl group or an amino group at the 2'-position of ribose;
(ii) an aptamer wherein PEG, amino acid, peptide, inverted dT, myristoyl, lithocolic-oleyl, docosanyl, lauroyl, stearoyl, palmitoyl, oleoyl, linoleoyl, other lipid, steroid, cholesterol, caffeine, vitamin, dye, a fluorescent substance, an anti-cancer agent, a toxin, an enzyme, a radioactive substance or biotin is added to the terminus;
(iii) an aptamer that satisfies the requirements of (i) and (ii); and the like.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a medicament or a diagnostic agent, a test drug, a reagent, an additive for drinking water and food, an enhancer and a mitigator.

The aptamer and complex of the present invention can have an activity to inhibit the function of MK by binding to MK and inhibiting the binding to cancer cell of MK. Therefore, the aptamer and complex of the present invention are useful as medicaments for the prophylaxis or treatment of cancer.

Examples of the cancer here include, but are not particularly limited to, those involving MK. Specifically, esophageal cancer, thyroid cancer, urinary bladder cancer, colorectal cancer, gastric cancer, pancreatic cancer, thoracic cancer, liver cancer, lung cancer, breast cancer, neuroblastoma, glioblastoma, uterine cancer, ovarian cancer, prostate cancer, Wilms' tumor and the like can be mentioned.

When bound with receptors such as receptor type protein tyrosine phosphatase ζ (PTPζ), LRP (low density lipoprotein receptor-related protein), ALK (anaplastic leukemia kinase), integrin, syndecan and the like, MK activates PI3K, MAPK and the like in the downstream, and exhibits physiological actions such as cell survival, growth and the like. Therefore, the aptamer and complex of the present invention can be used as medicaments, diagnostic agents, test drugs, or reagents for diseases relating to activation of these signal transduction pathways. Examples of the disease related to the activation of these signal transduction pathways include cancer, inflammatory disease, endometriosis, blood vessel obstructive disease, circulatory diseases and the like.

When the aptamer and complex of the present invention are used as medicaments, diagnostic agents, test drugs, reagents and the like, the subject of administration thereof is not particularly limited and, for example, primates (e.g., human, monkey), rodents (e.g., mouse, rat, guinea pig), and companion animals, domestic animals and working animals (e.g., dog, cat, horse, bovine, goat, sheep, swine) can be mentioned.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizinammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The medicament may be a rapid-release preparation or sustained-release preparation. Examples of sustained-release bases include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. Sustained-release preparations are also suitable preparations. The sustained-release preparations include sustained release from carriers or containers embedded in the body, such as artificial bones, biodegradable or non-degradable sponges, bags, drug pumps, osmotic pressure pumps and the like. Devices for continuous or intermittent, systemic or topical delivery from outside the body are also included in the scope of sustained-release preparations. Biodegradable bases include liposome, cationic liposome, poly(lactic-co-glycolic) acid (PLGA), atelocollagen, gelatin, hydroxyapatite, polysaccharide sizofiran. In addition to liquid injections and sustained release preparation, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydrofurfuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monooleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

EXAMPLES

The present invention is hereinafter described in more detail by means of the following Examples, which, however, never limit the scope of the invention.

The notation method of the aptamers is as follows. Small letters indicate DNA, and large letters indicate RNA. Parentheses in nucleotide show modification of the 2'-position of ribose, F shows fluorine atom, and M shows O-methyl group. For example, indication of G(M) means G wherein the 2'-position is modified by O-methyl group. idT shows inverted dT, 80PEG shows polyethylene glycol having a molecular weight of about 80000, 80PEG4ts shows SUNBRIGHT GL4-800TS manufactured by NOF CORPORATION, 80PEG4gs shows SUNBRIGHT GL4-800GS2, and 40PEG2ts shows use of SUNBRIGHT GL2-400TS.

Example 1

Production of MK Aptamer-1

An aptamer that specifically binds to MK (MK aptamer) was produced by the SELEX method. The SELEX method was an improved version of the method of Ellington et al. (Ellington and Szostak, Nature 346, 818-822, 1990) and the method of Tuerk et al. (Tuerk and Gold, Science 249, 505-510, 1990). As the target substance, human MK was prepared using yeast with reference to a method of Murasugi et al. (Murasugi and Tohma-Aiba, Protein Expression and Purification 27, 244-252, 2003). Hereinafter, unless otherwise specified, MK means human MK. MK was immobilized on an agarose resin (NHS-activated Sepharose, manufactured by Amersham Bioscience) by aminocoupling. The aminocoupling was performed as directed in the specifications of Amersham Bioscience. The amount immobilized was confirmed by examining the midkine solution just before immobilization and the supernatant just after immobilization by SDS-PAGE. As a result of the SDS-PAGE, no band of MK was detected in the supernatant; it was confirmed that nearly all of the MK used had been coupled. This means that about 175 g of midkine was immobilized to about 70 μL of the resin.

The RNA used in the first round (40N-RNA) was obtained by transcribing a chemically synthesized DNA using the DuraScribe™ T7 Transcription Kit (manufactured by Epicentre). The RNA obtained by this method has a fluorinated 2'-position of the ribose of the pyrimidine nucleotide. The DNA of 94 nucleotides shown below, having a primer sequence at each end of a 40-nucleotide random sequence (40n) was used as DNA template. The DNA template and the primers were prepared by chemical synthesis (manufactured by Operon).

DNA template:
(SEQ ID NO: 13)
5'-tcctcattcctgtcctcta-40n-ttcctcttctcctctccc-3' primer Fwd:
(SEQ ID NO: 14)
5'-taatacgactcactatagggagaggagaagaggaa-3' primer Rev:
(SEQ ID NO: 15)
5'-tcctcattcctgtcctcta-3' n is any one of a, g, c and t. The primer Fwd comprises a promoter sequence of T7 RNA polymerase. The variation of the RNA pool used in the first round was theoretically $10^{14}$.

The RNA pool was added to the MK-immobilized resin, and allowed to stand at room temperature for 30 minutes. After 30 minutes, to remove the RNA not bound to MK, the resin was washed with solution A. Here, the solution A was a mixed solution of 145 mM sodium chloride, 5.4 mM potassium chloride, 1.8 mM calcium chloride, 0.8 mM magnesium chloride, and 20 mM Tris (pH 7.6). The MK-bound RNA was recovered via heating at 95° C. for 10 minutes with the addition of an eluent. As the eluent, a mixed solution of 7 M urea, 3 mM EDTA, and 100 mM TRIS, adjusted to pH 6.6, was used. The recovered RNA was amplified by RT-PCR and transcribed using the DuraScribe™ T7 Transcription Kit, and this was used as the pool for the next round. With this procedure taken as 1 round, the same operation was performed in 7 rounds. After completion of SELEX, the PCR product was cloned into a pGEM-T Easy vector (manufactured by Promega), which was used to transform *Escherichia coli* strain DH5a (manufactured by Toyobo). The plasmid was extracted from a single colony and the base sequences of 48 clones were determined by DNA sequencer (ABI PRISM3100, manufactured by ABI).

After SELEX was performed in 7 rounds, the sequences were examined. As a result, 3 clones were converged, and 7 clones were single sequences. One of the single sequences is shown below.

SEQ ID NO: 1
GGGAGAGGAGAAGAGGAAGC(F)U(F)AU(F)C(F)GC(F)AAU(F)GG

U(F)GAGU(F)GGU(F)U(F)U(F)AU(F)C(F)C(F)GC(F)C(F)U (F)GC(F)GC(F)AU(F)GGU(F)U(F)AGAGGAC(F)AGGAAU(F)

GAGGA

The secondary structure of the oligonucleotide was predicted using the MFOLD program (Zuker, Nucleic Acids Res. 31, 3406-3415, 2003). The results are shown in FIG. 1.

Example 2

Production of MK Aptamer-2

SELEX similar to that in Example 1 was performed with a different DNA template and different primer sequences.

DNA template:
(SEQ ID NO: 16)
5'-ctctcatgtcggccgtta-40n-taacggccgacatgagag-3' primer Fwd:
(SEQ ID NO: 17)
5'-taatacgactcactatagggacacaatggacg-3' primer Rev:
(SEQ ID NO: 18)
5'-ctctcatgtcggccgtta-3' n is any one of a, g, c and t.

Figure 2:
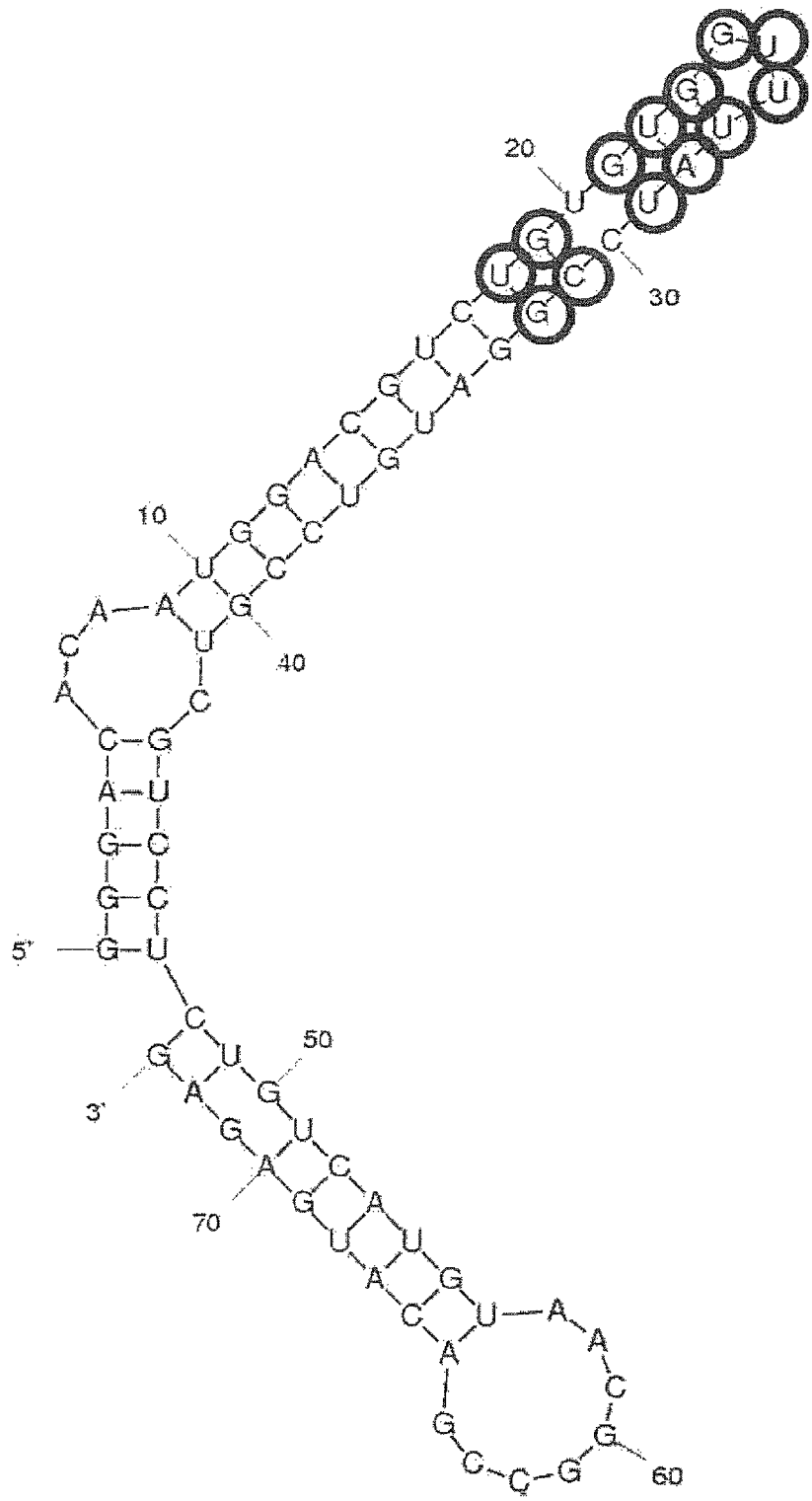
FIG. 2 shows a secondary structure prediction of the oligonucleotide shown in SEQ ID NO: 2.

After SELEX was performed in 13 rounds, the sequences of 48 clones were examined. As a result, 33 sequences shown in SEQ ID NO: 2, 3 sequences of 1-base substituted form thereof, and 1 sequence of 2-base substituted form thereof were present. The sequences (SEQ ID NOs: 2-6) of the obtained aptamers are shown below. They all contained the consensus sequence UGXGUGGUUUAUCCG (X=A or U; SEQ ID NO: 21) shown in SEQ ID NO: 1. The sequence is underlined. Using MFOLD program, the secondary structure was predicted. As a result, all consensus sequences showed the same secondary structure. As one embodiment of the secondary structure, FIG. 2 shows the results of the secondary structure prediction of the oligonucleotide shown in SEQ ID NO: 2.

SEQ ID NO: 2
GGGAC(F)AC(F)AAU(F)GGAC(F)GU(F)C(F)U(F)GU(F)GU(F)

GGU(F)U(F)U(F)AU(F)C(F)C(F)GGAU(F)GU(F)C(F)C(F)

GU(F)C(F)GU(F)C(F)C(F)U(F)C(F)U(F)GU(F)C(F)AU(F)

GU(F)AAC(F)GGC(F)C(F)GAC(F)AU(F)GAGAG

SEQ ID NO: 3
GGGAC(F)AC(F)AAU(F)GGAC(F)GU(F)C(F)U(F)GU(F)GU(F)

GGU(F)U(F)U(F)AU(F)C(F)C(F)GGAU(F)GU(F)C(F)C(F)

GU(F)C(F)GU(F)C(F)C(F)U(F)C(F)U(F)GU(F)C(F)GU(F)

GU(F)AAC(F)GGC(F)C(F)GAC(F)AU(F)GAGAG

SEQ ID NO: 4
GGGAC(F)AC(F)AAU(F)GGAC(F)GU(F)C(F)U(F)GU(F)GU(F)

GGU(F)U(F)U(F)AU(F)C(F)C(F)GGAU(F)GU(F)C(F)C(F)

GU(F)C(F)GU(F)C(F)C(F)U(F)C(F)U(F)GC(F)C(F)AU(F)

GU(F)AAC(F)GGC(F)C(F)GAC(F)AU(F)GAGAG

SEQ ID NO: 5
GGGAC(F)AC(F)AAU(F)GGAC(F)GU(F)C(F)U(F)GU(F)GU(F)

GGU(F)U(F)U(F)AU(F)C(F)C(F)GGAU(F)GU(F)C(F)C(F)

GU(F)C(F)GU(F)C(F)C(F)U(F)C(F)GGU(F)C(F)AU(F)GU (F)AAC(F)GGC(F)C(F)GAC(F)AU(F)GAGAG

SEQ ID NO: 6
GGGAC(F)AC(F)AAU(F)GGAC(F)GU(F)C(F)U(F)GU(F)GU(F)

GGU(F)U(F)U(F)AU(F)C(F)C(F)GGAC(F)GU(F)C(F)C(F)

GU(F)C(F)GU(F)C(F)C(F)U(F)C(F)U(F)GU(F)C(F)GU(F)

GU(F)AAC(F)GGC(F)C(F)GAC(F)AU(F)GAGAG

Example 3

Evaluation of Binding Activities by Surface Plasmon Resonance Method

The binding activities of the oligonucleotides shown by SEQ ID NO:1 to 6 obtained in Examples 1 and 2 for MK were evaluated by a surface plasmon resonance method. The measurements were performed using BIAcore2000, manufactured by BIAcore. The sensor chip used was the SA chip, which had streptavidin immobilized thereon. Bound thereto was about 1000 RU of a 16-nucleotide Poly dT with biotin bound to the 5' end thereof. The RNA being the ligand had a 16-nucleotide Poly A added to the 3' end thereof, and immobilized to the SA chip via a bond between dT and A. The amount immobilized was about 1000 RU. 70 µL of MK for analyte, prepared at 0.5 µM, was injected. The running buffer used for BIAcore was solution A. As a result of the measurements, it was found that all oligonucleotides strongly bind to MK.

Example 4

Shortening and Stabilization of MK Aptamer

Based on the aptamers shown in SEQ ID NOs: 1 and 2, short chaining was performed leaving the consensus sequence, whereby the aptamers shown in SEQ ID NOs: 7 and 8 were obtained from SEQ ID NOs: 1 and 2, respectively. To improve nuclease resistance of these short chained aptamers, O-methyl modification was performed at the 2'-position of ribose or idT modification was performed at the 3'-terminus. Furthermore, to improve in vivo pharmacokinetics, polyethylene glycol was added to the 5'-terminus.

Those aptamers were evaluated by the surface plasmon resonance method in the same manner as in Example 3, and they were confirmed to have MK binding activity.

The short chained and stabilized aptamers were chemically synthesized by the phosphoramidite method. This synthesis method is generally used frequently, and as described in Oligonucleotide Synthesis Methods and Applications (Editor: Piet Herdewijn, Humana Press) and the like. In fact, it was synthesized using a nucleic acid synthesizer (ABI394) manufactured by Applied Biosystems, and purified by the high performance liquid chromatography method (HPLC). The purity of the final synthesized substance was determined by HPLC, and not less than 85% was acceptable. It was also confirm by MALDI-TOFMS that the molecular weight is identical with the theoretical molecular weight.

An aptamer wherein a polyethylene glycol chain (PEG) is added to the 5'-terminus was synthesized as follows. First, an aptamer wherein an amino group is added to the 5'-terminus was synthesized using the above-mentioned nucleic acid synthesizer. After purification by HPLC, the aptamer was analyzed by HPLC and MALDI-TOFMS to confirm a purity of not less than 85%. Then, the aptamers were mixed with PEG added with an active group of N-hydroxysuccinimide, and a coupling reaction was performed at room temperature. After the reaction, purification and purity analysis were performed by HPLC. A final purity of not less than 85% was acceptable.

The nucleotide sequences of aptamers shown in SEQ ID NOs: 7 and 8, which were actually produced, are shown below.

```
                                       SEQ ID NO: 7
GC(F)C(F)AU(F)C(F)GC(F)AAU(F)GGU(F)GAGU(F)GGU(F)U (F)U(F)AU(F)C(F)C(F)GC(F)C(F)U(F)GC(F)GC(F)AU(F)

GGC(F)
```

```
                                       SEQ ID NO: 7-1
G(M)C(M)C(M)AU(F)C(F)GC(F)AAU(F)GGU(F)GAGU(F)GGU (F)U(F)U(F)AU(F)C(F)C(F)GC(F)C(F)U(F)GC(F)GC(F)AU (F)G(M)G(M)C(M)
```

```
                                       SEQ ID NO: 8
GU(F)C(F)U(F)GU(F)GU(F)GGU(F)U(F)U(F)AU(F)C(F)C (F)GGAC(F)
```

```
                                       SEQ ID NO: 8-1
G(M)U(F)C(F)U(F)GU(F)GU(F)G(M)G(M)U(F)U(F)U(M)AU (F)C(F)C(F)G(M)G(M)A(M)C(F)
```

```
                                       SEQ ID NO: 8-2
80PEG4ts-
G(M)U(F)C(F)U(F)GU(F)GU(F)G(M)G(M)U(F)U(F)U(M)AU (F)C(F)C(F)G(M)G(M)A(M)C-idT
```

```
                                       SEQ ID NO: 8-3
80PEG4gs-
G(M)U(F)C(F)U(F)GU(F)GU(F)G(M)G(M)U(F)U(F)U(M)AU (F)C(F)C(F)G(M)G(M)A(M)C-idT
```

```
                                       SEQ ID NO: 8-4
80PEG4ts-
G(M)U(M)C(M)U(F)GU(F)GU(M)G(M)G(M)U(F)U(F)U(M)AU (F)C(F)C(F)G(M)G(M)A(M)C(M)-idT
```

```
                                       SEQ ID NO: 8-5
80PEG4gs-
G(M)U(M)C(M)U(F)GU(F)GU(M)G(M)G(M)U(F)U(F)U(M)AU (F)C(F)C(F)G(M)G(M)A(M)C(M)-idT
```

Example 5

Confirmation of Binding Inhibitory Activity by AP-MK Assay

Whether MK aptamer can inhibit MK from binding to cancer cells was examined. To detect binding of MK and cancer cell, MK protein bound with alkaliphosphatase (AP-MK) was used.

AP-MK was produced as follows. MK cDNA free of signal sequence (Lys23-stop) was inserted into XhoI-XbaI site of APtag-5 vector (manufactured by GenHunter). 293T cells were plated at $2.0 \times 10^6$ cells/10 cm dish, and APtag-5, and APtag-5-MK plasmid (7.5 µg) were transfected the next day using FuGENE6 (manufactured by Roche) (15 µL). As the medium, OPTI-MEM I (1% ITSA) was used, and the protocol attached to FuGENE6 was followed. Five days later, the medium was recovered in Proteosave SS (SUMITOMO BAKELITE), centrifuged at 1500 rpm for 5 min, and passed though a 0.22 µm PVDF filter. 2 µL was measured, MilliQ 48 µL, AP Assay Reagent A (manufactured by GenHunter) (50 µL) were added, and the mixture was allowed to develop color at 37° C. for 10 min. 0.5N NaOH (100 µL) was added to stop the color development, and MilliQ (800 µL) was added. $OD_{405}$ was measured and the activity was measured by the following formula.

[U/mL]=$OD_{405}$×54/(10 min×2 µL)

Using the above-mentioned AP-MK, a binding inhibitory experiment relative to TNB1 cell, which is a human neuroblastoma cell, was performed. TNB1 cells were seeded at $1 \times 10^5$ cells/well on a 6-well plate coated with collagen I.

The next day, the cells were washed with 1 mL of HBHA (HBSS+0.5 mg/mL BSA+20 mM HEPES pH 7.0), 1 U/mL AP or AP-MK, and further, the aptamer shown in SEQ ID NO: 7-1 at a final concentration of 100 nM were added and the mixture was maintained at room temperature for 90 min. After washing 5 times with 1 mL of HBHA, 200 µL of Cell Lysis Buffer (manufactured by GenHunter) was added and the mixture was stirred for 5 min. The cells were scraped with a Scraper and placed in an Eppendorf tube, vortexed for 10 sec and centrifuged at 15000 rpm for 2 min. The supernatant was recovered, and heated at 65° C. for 10 min to inactivate endogenous AP. Using 50 µL, color development was performed in the same manner as above (15 min) and the activity of AP was calculated.

[U/mL]=$OD_{405}$×54/(15 min×50 µL)

Figure 3:
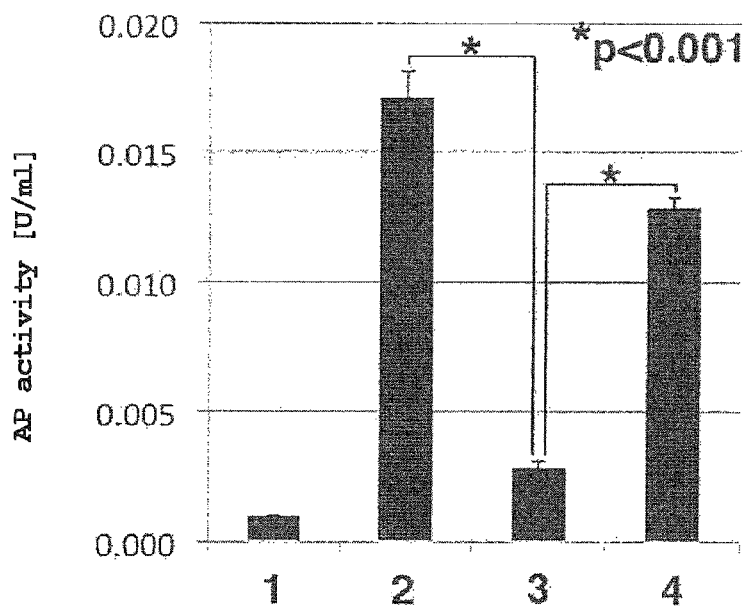
FIG. 3 shows the results of binding inhibitory experiments of AP-MK and TNB1 cells. 1) AP alone, 2) AP-MK alone, 3) AP-MK and aptamer shown in SEQ ID NO: 7-1, 4) AP-MK and a negative control shown in SEQ ID NO: 19.

AP-MK was bound to TNB1 cell surface, and the binding thereof was inhibited by 82% by 100 nM aptamer shown in SEQ ID NO: 7-1. On the other hand, the inhibitory effect was significantly small in the negative control RNA shown in SEQ ID NO: 19 as compared to the aptamer shown in SEQ ID NO: 7-1. Therefore, the specificity of the aptamer shown in SEQ ID NO: 7-1 was shown (FIG. 3).

SEQ ID NO: 19
G(M)C(M)C(M)AU(F)GGU(F)GGU(F)C(F)AAC(F)C(F)GU(F)

C(F)GGU(F)AU(F)U(F)GC(F)C(F)GC(F)AGU(F)U(F)AC(F)

U(F)G(M)G(M)C(M)

An experiment similar to the above was performed using MEF-1 cells which are mouse embryonic fibroblasts. As a result, it was found that the aptamer shown in SEQ ID NO: 7-1 inhibits the binding of AP-MK and MEF-1 cell by not less than 90% at 100 nM.

An experiment similar to the above was performed using HepG2 cells which are human liver cancer-derived cells. It is already known that MK is deeply involved in the growth and inhibition of apoptosis of HepG2 cells (Ohuchida et al., Cancer 100, 2430-2436, 2004; Dai et al., World J. Gastroenterol. 15, 1966-1972, 2009). When the aptamer was added to the system, the binding of AP-MK and HepG2 was inhibited (Table 1).

TABLE 1

Table 1 Results of AP-MK assay using HepG2 cells. Inhibitory % by the addition of 500 nM aptamer is shown.

| aptamer (500 nM) | inhibitory % |
|---|---|
| SEQ ID NO: 7-1 | 93 |
| SEQ ID NO: 8-1 | 76 |
| SEQ ID NO: 8-2 | 61 |
| SEQ ID NO: 8-3 | 65 |
| SEQ ID NO: 8-4 | 58 |
| SEQ ID NO: 8-5 | 61 |

An altered form of SEQ ID NO: 7-1 was produced, and AP-MK binding inhibitory experiment was performed using HepG2 and TNB1 cells and in the same manner as above. The sequences of the altered forms actually produced are shown below. While Poly dA for BIAcore measurement is added to the 3'-terminus of the aptamers shown in SEQ ID NO: 9 and SEQ ID NO: 9-1-5, an influence on the activity is not expected. The 50% inhibitory concentration ($IC_{50}$) was determined from the concentrations at two, above and below points sandwiching the 50% inhibitory activity (Table 2).

SEQ ID NO: 7-2
40PEG2ts-
G(M)C(M)C(M)AU(F)C(F)GC(F)AAU(F)GG<u>U(F)GAGU(F)GGU</u>

<u>(F)U(F)U(F)AU(F)C(F)C(F)GC</u>(F)C(F)U(F)GC(F)GC(F)AU (F)G(M)G(M)C(M)-idT

SEQ ID NO: 7-3
40PEG2ts-
G(M)C(M)C(M)A(M)U(M)C(M)G(M)C(M)A(M)A(M)U(M)G(M)

G(M)<u>U(F)GAGU(F)G(M)G(M)U(F)U(F)U(M)AU(F)C(F)C(F)</u>

<u>G(M)</u>C(F)C(M)U(M)G(M)C(M)G(M)C(M)A(M)U(M)G(M)

C(M)-idT

SEQ ID NO: 7-4
40PEG2ts-
G(M)C(M)C(M)A(M)U(F)C(F)G(M)C(F)A(M)A(M)U(F)G(M)

G(M)<u>U(F)GAGU(F)G(M)G(M)U(F)U(F)U(F)AU(F)C(F)C(F)</u>

<u>G(M)</u>C(F)C(F)U(F)G(M)C(F)G(M)C(F)A(M)U(F)G(M)G(M)

C(M)-idT

SEQ ID NO: 7-5
G(M)C(M)C(M)A(M)U(M)C(M)G(M)C(M)A(M)A(M)U(M)G(M)

G(M)<u>U(F)GA(M)GU(F)G(M)G(M)U(F)U(F)U(M)AU(F)C(F)</u>

<u>C(F)G(M)</u>C(F)C(M)U(M)G(M)C(M)G(M)C(M)A(M)U(M)G(M)

G(M)C(M)-idT

SEQ ID NO: 7-6
G(M)C(M)C(M)A(M)U(M)C(M)G(M)C(M)A(M)A(M)U(M)G(M)

G(M)<u>U(M)GA(M)GU(F)G(M)G(M)U(F)U(F)U(M)AU(F)C(F)</u>

<u>C(F)G(M)</u>C(F)C(M)U(M)G(M)C(M)G(M)C(M)A(M)U(M)G(M)

G(M)C(M)-idT

SEQ ID NO: 7-7
G(M)C(M)C(M)A(M)U(M)C(M)G(M)C(M)A(M)A(M)U(M)G(M)

G(M)<u>U(F)GA(M)GU(F)G(M)G(M)U(F)U(F)U(M)AU(F)C(F)</u>

C(M)G(M)C(F)C(M)U(M)G(M)C(M)G(M)C(M)A(M)U(M)G(M)

G(M)C(M)-idT

SEQ ID NO: 7-8
G(M)C(M)C(M)A(M)U(M)C(M)G(M)C(M)A(M)A(M)U(M)G(M)

G(M)<u>U(F)GA(M)GU(F)G(M)G(M)U(F)U(F)U(M)AU(F)C(F)C</u>

<u>(F)G(M)</u>C(M)C(M)U(M)G(M)C(M)G(M)C(M)A(M)U(M)G(M)G (M)C(M)-idT

SEQ ID NO: 7-9
G(M)C(M)C(M)A(M)U(M)C(M)G(M)C(M)A(M)A(M)U(M)G(M)

G(M)<u>U(F)GA(M)G(M)U(F)G(M)G(M)U(F)U(F)U(M)AU(F)C</u>

<u>(F)C(F)G(M)</u>C(F)C(M)U(M)G(M)C(M)G(M)C(M)A(M)U(M)

G(M)G(M)C(M)-idT

SEQ ID NO: 9 (with polyA added to the terminal of SEQ ID NO: 7-1)
G(M)C(M)C(M)AU(F)C(F)GC(F)AAU(F)GG<u>U(F)GAGU(F)GGU</u>

<u>(F)U(F)U(F)AU(F)C(F)C(F)GC</u>(F)C(F)U(F)GC(F)GC(F)

AU(F)G(M)G(M)C(M)aaaaaaaaaaaaaaaa

-continued

SEQ ID NO: 9-1
G(M)C(M)C(M)A(M)U(F)C(F)G(M)C(F)A(M)A(M)U(F)G(M)G (M)U(F)GAGU(F)G(M)G(M)U(F)U(F)U(F)AU(F)C(F)C(F)G (M)C(F)C(F)U(F)G(M)C(F)G(M)C(F)A(M)U(F)G(M)G(M)C (M)aaaaaaaaaaaaaaa

SEQ ID NO: 9-2
G(M)C(M)C(M)A(M)U(F)C(F)G(M)C(F)A(M)A(M)U(F)G(M)G (M)U(F)G(M)AGU(F)G(M)G(M)U(F)U(F)U(F)AU(F)C(F)C (F)G(M)C(F)C(F)U(F)G(M)C(F)G(M)C(F)A(M)U(F)G(M)G (M)C(M)aaaaaaaaaaaaaaa

SEQ ID NO: 9-3
G(M)C(M)C(M)A(M)U(F)C(F)G(M)C(F)A(M)A(M)U(F)G(M)G (M)U(F)GA(M)GU(F)G(M)G(M)U(F)U(F)U(F)AU(F)C(F)C(F)

G(M)C(F)C(F)U(F)G(M)C(F)G(M)C(F)A(M)U(F)G(M)G(M)C (M)aaaaaaaaaaaaaaa

SEQ ID NO: 9-4
G(M)C(M)C(M)A(M)U(F)C(F)G(M)C(F)A(M)A(M)U(F)G(M)G (M)U(F)GAG(M)U(F)G(M)G(M)U(F)U(F)U(F)AU(F)C(F)C(F)

G(M)C(F)C(F)U(F)G(M)C(F)G(M)C(F)A(M)U(F)G(M)G(M)C (M)aaaaaaaaaaaaaaa

SEQ ID NO: 9-5
G(M)C(M)C(M)A(M)U(F)C(F)G(M)C(F)G(M)C(F)A(M)A(M)U(F)G(M)G (M)U(F)GAGU(F)G(M)G(M)U(F)U(F)U(F)A(M)U(F)C(F)C(F)

G(M)C(F)C(F)U(F)G(M)C(F)G(M)C(F)A(M)U(F)G(M)G(M)C (M)aaaaaaaaaaaaaaa

SEQ ID NO: 10 (SEQ ID NO: 7-3 without
2 base pairs(4 nucleotides) and PEG)
G(M)C(M)U(M)C(M)G(M)C(M)A(M)A(M)U(M)G(M)G(M)U(F)

GAGU(F)G(M)G(M)U(F)U(F)U(M)AU(F)C(F)C(F)G(M)C(F)

C(M)U(M)G(M)C(M)G(M)C(M)A(M)G(M)C(M)-idT

SEQ ID NO: 11 (SEQ ID NO: 7-6 without
terminal 11 nucleotides and added
with G-C pair)
G(M)C(M)G(M)C(M)A(M)A(M)U(M)G(M)G(M)U(M)GA(M)GU (F)G(M)G(M)U(F)U(F)U(M)AU(F)C(F)C(F)G(M)C(F)C(M)

U(M)G(M)C(M)G(M)C(M)-idT

SEQ ID NO: 11-1
G(M)C(M)G(M)C(M)A(M)A(M)U(M)G(M)G(M)U(M)GA(M)GU (F)G(M)G(M)U(F)U(F)U(M)AU(F)C(F)C(M)G(M)C(M)C(M)

U(M)G(M)C(M)G(M)C(M)-idT

SEQ ID NO: 12 (SEQ ID NO: 7-3 without
terminal 11 nucleotides and PEG)
C(M)G(M)C(M)A(M)A(M)U(M)G(M)G(M)G(M)U(F)GAGU(F)G(M)

G(M)U(F)U(F)U(M)AU(F)C(F)C(F)G(M)C(F)C(M)U(M)G (M)C(M)G(M)-idT

TABLE 2

Table 2 Results of AP-MK assay. Concentration of aptamer at inhibitory rate 50% (IC50).

| aptamer | TNB1 IC50 (nM) | HepG2 IC50 (nM) |
|---|---|---|
| SEQ ID NO: 7-1 | 18 | 6.0 |
| SEQ ID NO: 7-2 | 26 | 4.9 |
| SEQ ID NO: 7-3 | 11 | 1.7 |
| SEQ ID NO: 7-4 | 18 | 3.6 |
| SEQ ID NO: 7-5 | n.d. | <2 |
| SEQ ID NO: 7-6 | n.d. | <2 |
| SEQ ID NO: 7-7 | n.d. | <2 |
| SEQ ID NO: 7-8 | n.d. | <2 |
| SEQ ID NO: 7-9 | n.d. | 4.7 |
| SEQ ID NO: 9 | n.d. | 3.3 |
| SEQ ID NO: 9-1 | n.d. | 1.6 |
| SEQ ID NO: 9-2 | n.d. | 13 |
| SEQ ID NO: 9-3 | n.d. | 3.0 |
| SEQ ID NO: 9-4 | n.d. | 4.1 |
| SEQ ID NO: 9-5 | n.d. | 19 |
| SEQ ID NO: 10 | n.d. | <2 |
| SEQ ID NO: 11 | n.d. | 6.3 |
| SEQ ID NO: 11-1 | n.d. | 7.8 |
| SEQ ID NO: 12 | n.d. | <2 | n.d. means not determined.

Figure 4:
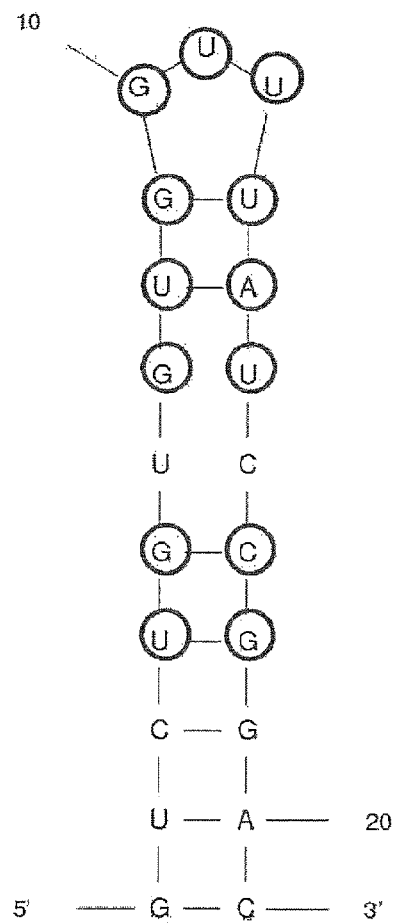
FIG. 4 shows a secondary structure prediction of the oligonucleotide shown in SEQ ID NO: 8.

The 21 mer aptamer shown in SEQ ID NO: 8-1 showed high inhibitory activity. Its secondary structure was predicted using a MFOLD program. The results are shown in FIG. 4. The sequence shown with a circle (O) and the secondary structure are contained in all aptamers shown in SEQ ID NOs: 1-12, and are considered the consensus sequence relating to the activity. The sequence is shown below.

```
                                    (SEQ ID NO: 20)
(X1)(X2)UG(X3)GUGGUUUAU(X4)CG(X5)(X6)
```

Here, nucleotides X1 and X6, and X2 and X5 on the terminal portions each form base pairs. X1-X6 may be any of A, G, C and U. In addition, U may be T.

While the aptamers shown in SEQ ID NO: 7-3 and 8-2 have different modifications at the 2'-position of ribose from that of the aptamer shown in SEQ ID NO: 7 or 8, they showed high inhibitory activity. Also, they maintained the activity even when the 5'-terminus was modified with polyethylene glycol, and the 3'-terminus was modified with idT. The foregoing has clarified that the aptamer can maintain activity even when the 2'-position or terminal of ribose is modified.

Example 6

Soft Agar Assay Using TNB1 Cells

First, whether TNB1 cell produces MK was confirmed by Western blotting. TNB1 cells were cultured in RPMI1640 medium added with 10% FBS under the conditions of 37° C., 5% $CO_2$. The obtained culture supernatant was centrifuged at 3000 rpm for 5 min, the cells were removed, and the residue was centrifuged at 15000 rpm for 30 min. Insoluble materials were removed and the residue was subjected to SDS-PAGE (7.5% polyacrylamide gel). Protein after electrophoresis was transferred onto a PVDF membrane (manufactured by Millipore), and the membrane was blocked with a blocking solution (5% skim milk, 0.05% Tween 20, PBS) for 1 hr, and reacted in the blocking solution added with a mouse anti-MK antibody for not less than 2 hr at room temperature. Thereafter, the membrane was washed twice with a washing (0.05% Tween20, PBS), and reacted in the blocking solution added with an HRP-labeled anti-mouse IgG antibody at room temperature for 1 hr. After the reaction, the membrane was washed three times with a washing, and detected by LAS-4000mini EPUV (manufactured by Fujifilm Corporation) and using ECL Plus Western Blotting Detection System (Amersham Pharmacia Biotech). As a result, it could be confirmed that MK was produced from TNB1 cells used.

Using the cells, a soft agar assay was performed. 1.5 mL of bottom agar (0.5% agar/RPMI-1640/10% FBS) was added to a 6-well plate, and maintained at room temperature for 30 min. A top agar (0.33% agar/RPMI-1640/10% FBS) (1 mL) added with TNB1 cells (2000 cells/well) and an aptamer at a final concentration of 100 nM was added onto the bottom agar. After 3 weeks of culture, the cells were stained with crystal violet, 6 fields were photographed per each well and colony was counted.

Figure 5:
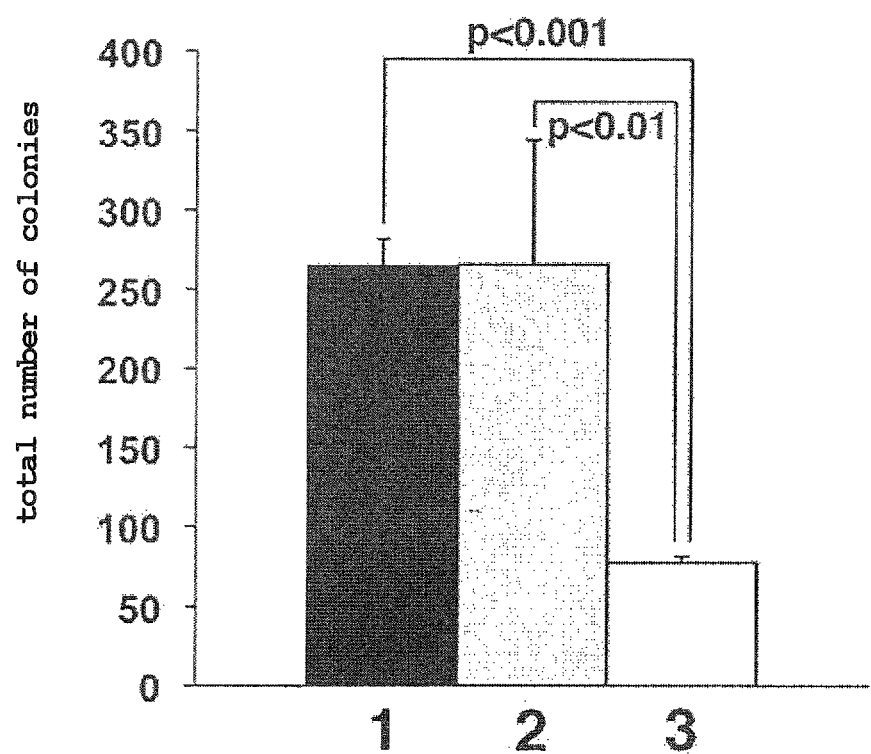
FIG. 5 shows the results of a soft agar assay using TNB1 cells. 1) aptamer no-addition group, 2) a group added with the negative control shown in SEQ ID NO: 24, 3) a group added with the aptamer shown in SEQ ID NO: 7-1.

The colony number of TNB1 cells significantly decreased in the presence of the aptamer shown in SEQ ID NO: 7-1, as compared to the control without addition (FIG. 5). On the other hand, when the negative control shown in SEQ ID NO: 19 was added, the number was of the same level as that of the control, which shows that the anchorage independent growth inhibitory action of the aptamer shown in SEQ ID NO: 7-1 is specific.

Example 7

Evaluation of MK Aptamers by Cell Migration Inhibition Experiment

Midkine is known to possess osteoblast progenitor cell infiltrating action (Qi et al., J. Biol. Chem. 276 (19), 15868-15875, 2001). Hence, it was examined whether or not the prepared MK aptamers inhibited the cell migration activity of midkine using UMR106 cells of a rat osteoblast progenitor cell line (ATCC No. CRL1661). 30 μL of 1.5 μM midkine was applied to the outer surface of the membrane of Chemotaxicell (membrane pore diameter 8 μm, manufactured by Kurabo) to immobilize the midkine to the outer surface of the membrane. The midkine-immobilized Chemotaxicell was placed on a 24-well culture plate containing 500 μL of a medium (supplemented with 0.3% bovine serum albumin, Dulbecco's Modified Eagle's medium) supplemented with each RNA aptamer added thereto at 100 nM. 200 μL of UMR106 cells were placed in the inner layer of the Chemotaxicell chamber at a density of 1×10$^6$ cells/mL, and cultured at 37° C. for 4 hours. The cells remaining in the inner layer of the Chemotaxicell chamber were removed, and the cells that had infiltrated and adhered to the midkine-applied surface were fixed with methanol. The Chemotaxicell chamber was immersed in a 1% aqueous solution of Crystal Violet for 30 minutes to stain the cells. After the Chemotaxicell chamber was washed with distilled water and dried, the pigment was extracted with a mixed solution of 200 μL of 1% SDS and 1% triton X100. 150 μL of the extract was transferred to a 96-well microplate, and its absorbance at 590 nm was determined.

As a result of the measurement, remarkable inhibition of cell migration was not observed when the aptamer shown in SEQ ID NO: 7-1 was added at 500 nM. On the other hand, when the aptamer shown in SEQ ID NO: 45-4-1 described in WO 2008/059877 was used, IC50 was 44 nM. When the aptamer shown in SEQ ID NO: 7 described in WO 2009/063998 was used, IC50 was 13 nM. From the above, it was found that the aptamer described in the present specification is different from the aptamers described in WO 2008/059877 and WO 2009/063998, since it does not have a cell migration inhibitory capacity.

Example 8

Cancer-Bearing Mouse Model Using TNB1 Cells

Equal amounts of TNB1 cells and Matrigel (BD Biosciences) were mixed, and 200 μL (10000 cells) was subcutaneously transplanted to the abdomen of KSN nude mouse. From 3 weeks later when the tumor reaches a diameter of about 5 mm, 100 μg of an aptamer per tumor was intratumorally administered twice a week, 8 times in total. The volume of the tumor was measured once a week (width× width×length/2), the mouse was euthanized at 4 weeks from the first administration, and the weight of the tumor was measured.

Figure 6:
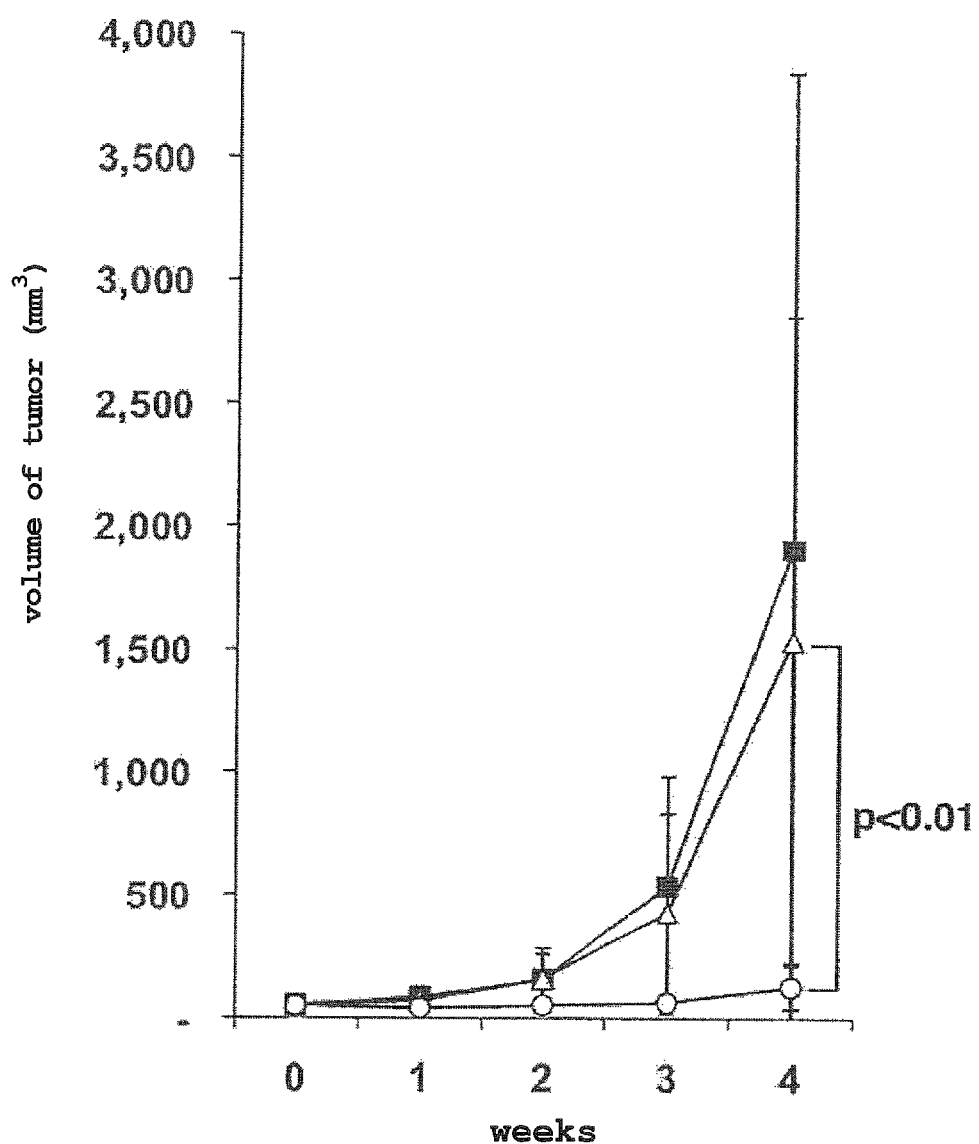
FIG. 6 shows the results of a cancer-carrying mouse model experiment using TNB1 cells. square (■): solvent administration group, triangle (∆): negative control administration group shown in SEQ ID NO: 19, circle (○): aptamer administration group shown in SEQ ID NO: 7-1.

While the tumor volume rapidly increased in the solvent administration group and the negative control (shown in SEQ ID NO: 19) administration group, the tumor volume remained almost flat in the aptamer (shown in SEQ ID NO: 7-1) administration group, and the growth was remarkably suppressed (FIG. 6). Similarly, when compared with the solvent administration group and the negative control (shown in SEQ ID NO: 19) administration group, the weight of the tumor at 4 weeks from the start of the treatment was significantly smaller in the aptamer (shown in SEQ ID NO: 7-1) administration group. From the above, it was shown that the aptamer provided by the present invention is utilizable as a therapeutic drug for cancer involving MK.

INDUSTRIAL APPLICABILITY

Since the aptamer or nucleic acid of the present invention has a superior MK activity inhibitory action, particularly, a superior action in the inhibition of the binding activity of MK to cancer cells, it can be useful as a therapeutic drug for cancer.

This application is based on a patent application No. 2012-255588 filed in Japan (filing date: Nov. 21, 2012), the contents of which are incorporated in full herein.

The invention claimed is:

1. An aptamer binding to midkine having a length of not more than 45 nucleotides and capable of forming a potential secondary structure represented by the formula (I):

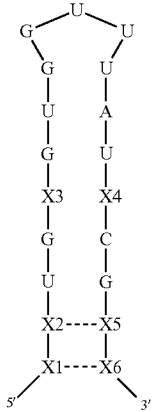

wherein

X1, X2, X5 and X6 are the same or different and each is one or two nucleotides selected from the group consisting of A, G, C, U and T, or a bond, X1 and X6, and X2 and X5 each form a Watson-Crick base pairs, and X3 and X4 are the same or different and each is a nucleotide selected from A, G, C, U and T.

2. The aptamer according to claim 1, wherein X1, X2, X5 and X6 are the same or different and each is one nucleotide selected from the group consisting of A, G, C, U and T.

3. The aptamer according to claim 1, wherein X3 is A or U, and X4 is C.

4. An isolated nucleic acid having a length of 15 to 100 nucleotides and comprising a nucleic acid of any of the following (a) (c):

(a) a nucleic acid defined as any of SEQ ID NOs: 1-12 and 20;

(b) the nucleic acid of the above-mentioned (a), wherein one to three nucleotides are substituted, deleted, inserted or added, which binds to midkine;

(c) the nucleic acid of the above-mentioned (a) or (b), wherein a group at the 2'-position of ribose of one or plural nucleotides is substituted by other group.

5. The aptamer according to claim 1, wherein at least one nucleotide is modified.

6. The aptamer according to claim 5, which is modified with inverted dT or polyethylene glycol.

7. The aptamer according to claim 6, wherein inverted dT or polyethylene glycol is bonded to either or both of the 5'- and 3'-termini of the aptamer or nucleic acid.

8. The aptamer according to claim 5, wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group; and/or
wherein the hydroxyl groups at the 2'-position of a ribose of respective purine nucleotides are the same or different and unreplaced or replaced by an atom or group selected from the group consisting of a hydrogen atom, a fluorine atom and a methoxy group.

9. The aptamer according to claim 1, which inhibits binding of midkine to a cancer cell and/or midkine-dependent cell proliferation.

10. A pharmaceutical composition comprising:
(a) the aptamer according to claim 1; or
(b) an isolated nucleic acid having a length of 15 to 100 nucleotides and comprising a nucleic acid of any of the following (i)-(iii):
(i) a nucleic acid defined as any of SEQ ID NOs: 1-12 and 20;
(ii) the nucleic acid of the above-mentioned (i), wherein one to three nucleotides are substituted, deleted, inserted or added, which binds to midkine;
(iii) the nucleic acid of the above-mentioned (i) or (ii), wherein a group at the 2'-position of ribose of one or plural nucleotides is substituted by other group.

11. A therapeutic drug for cancer comprising:
(a) the aptamer according to claim 1; or
(b) an isolated nucleic acid having a length of 15 to 100 nucleotides and comprising a nucleic acid of any of the following (i)-(iii):
(i) a nucleic acid defined as any of SEQ ID NOs: 1-12 and 20;
(ii) the nucleic acid of the above-mentioned (i), wherein one to three nucleotides are substituted, deleted, inserted or added, which binds to midkine;
(iii) the nucleic acid of the above-mentioned (i) or (ii), wherein a group at the 2'-position of ribose of one or plural nucleotides is substituted by other group.

12. The nucleic acid according to claim 4, which has a nucleotide length of not more than 45.

13. The nucleic acid according to claim 4, wherein at least one nucleotide is modified.

14. The nucleic acid according to claim 13, which is modified with inverted dT or polyethylene glycol.

15. The nucleic acid according to claim 14, wherein inverted dT or polyethylene glycol is bonded to either or both of the 5'- and 3'-termini of the aptamer or nucleic acid.

16. The nucleic acid according to claim 13, wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group; and/or
wherein the hydroxyl groups at the 2'-position of a ribose of respective purine nucleotides are the same or different and unreplaced or replaced by an atom or group selected from the group consisting of a hydrogen atom, a fluorine atom and a methoxy group.

17. The nucleic acid according to claim 4, which inhibits binding of midkine to a cancer cell and/or midkine-dependent cell proliferation.

* * * * *

SEQUENCE LISTING

```
<160> NUMBER OF SEQ ID NOS: 21

<210> SEQ ID NO 1
<211> LENGTH: 77
<212> TYPE: RNA
<213> ORGANISM: Artificial Sequence
<220> FEATURE:
<223> OTHER INFORMATION: Aptamer against midkine
```

```
<400> SEQUENCE: 1
gggagaggag aagaggaagc uaucgcaaug gugagugguu uauccgccug cgcaugguua    60
gaggacagga augagga                                                  77

<210> SEQ ID NO 2
<211> LENGTH: 73
<212> TYPE: RNA
<213> ORGANISM: Artificial Sequence
<220> FEATURE:
<223> OTHER INFORMATION: Aptamer against midkine

<400> SEQUENCE: 2
gggacacaau ggacgucugu gugguuuauc cggauguccg ucguccucug ucauguaacg    60
gccgacauga gag                                                      73

<210> SEQ ID NO 3
<211> LENGTH: 73
<212> TYPE: RNA
<213> ORGANISM: Artificial Sequence
<220> FEATURE:
<223> OTHER INFORMATION: Aptamer against midkine

<400> SEQUENCE: 3
gggacacaau ggacgucugu gugguuuauc cggauguccg ucguccucug ucguguaacg    60
gccgacauga gag                                                      73

<210> SEQ ID NO 4
<211> LENGTH: 73
<212> TYPE: RNA
<213> ORGANISM: Artificial Sequence
<220> FEATURE:
<223> OTHER INFORMATION: Aptamer against midkine

<400> SEQUENCE: 4
gggacacaau ggacgucugu gugguuuauc cggauguccg ucguccucug ccauguaacg    60
gccgacauga gag                                                      73

<210> SEQ ID NO 5
<211> LENGTH: 73
<212> TYPE: RNA
<213> ORGANISM: Artificial Sequence
<220> FEATURE:
<223> OTHER INFORMATION: Aptamer against midkine

<400> SEQUENCE: 5
gggacacaau ggacgucugu gugguuuauc cggauguccg ucguccucgg ucauguaacg    60
gccgacauga gag                                                      73

<210> SEQ ID NO 6
<211> LENGTH: 73
<212> TYPE: RNA
<213> ORGANISM: Artificial Sequence
<220> FEATURE:
<223> OTHER INFORMATION: Aptamer against midkine

<400> SEQUENCE: 6
gggacacaau ggacgucugu gugguuuauc cggacguccg ucguccucug ucguguaacg    60
gccgacauga gag                                                      73

<210> SEQ ID NO 7
```

```
<211> LENGTH: 40
<212> TYPE: RNA
<213> ORGANISM: Artificial Sequence
<220> FEATURE:
<223> OTHER INFORMATION: Aptamer against midkine

<400> SEQUENCE: 7
gccaucgcaa uggugagugg uuuauccgcc ugcgcauggc                                40

<210> SEQ ID NO 8
<211> LENGTH: 21
<212> TYPE: RNA
<213> ORGANISM: Artificial Sequence
<220> FEATURE:
<223> OTHER INFORMATION: Aptamer against midkine

<400> SEQUENCE: 8
gucugugugg uuuauccgga c                                                   21

<210> SEQ ID NO 9
<211> LENGTH: 56
<212> TYPE: RNA
<213> ORGANISM: Artificial Sequence
<220> FEATURE:
<223> OTHER INFORMATION: Aptamer against midkine

<400> SEQUENCE: 9
gccaucgcaa uggugagugg uuuauccgcc ugcgcauggc aaaaaaaaaa aaaaaa            56

<210> SEQ ID NO 10
<211> LENGTH: 36
<212> TYPE: RNA
<213> ORGANISM: Artificial Sequence
<220> FEATURE:
<223> OTHER INFORMATION: Aptamer against midkine

<400> SEQUENCE: 10
gcucgcaaug gugagugguu uauccgccug cgcagc                                   36

<210> SEQ ID NO 11
<211> LENGTH: 31
<212> TYPE: RNA
<213> ORGANISM: Artificial Sequence
<220> FEATURE:
<223> OTHER INFORMATION: Aptamer against midkine

<400> SEQUENCE: 11
gcgcaauggu gagugguuua uccgccugcg c                                        31

<210> SEQ ID NO 12
<211> LENGTH: 29
<212> TYPE: RNA
<213> ORGANISM: Artificial Sequence
<220> FEATURE:
<223> OTHER INFORMATION: Aptamer against midkine

<400> SEQUENCE: 12
cgcaauggug agugguuuau ccgccugcg                                           29

<210> SEQ ID NO 13
<211> LENGTH: 78
<212> TYPE: DNA
<213> ORGANISM: Artificial Sequence
<220> FEATURE:
<223> OTHER INFORMATION: DNA template
<220> FEATURE:
<221> NAME/KEY: misc_feature
```

```
<222> LOCATION: (20)..(59)
<223> OTHER INFORMATION: n is a, c, g, or t

<400> SEQUENCE: 13
tcctcattcc tgtcctctan nnnnnnnnnn nnnnnnnnnn nnnnnnnnnn nnnnnnnnt      60 ttcctcttct cctctccc                                                   78

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
taatacgact cactataggg agaggagaag aggaa                                35

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
tcctcattcc tgtcctcta                                                  19

<210> SEQ ID NO 16
<211> LENGTH: 76
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (19)..(58)
<223> OTHER INFORMATION: n is a, c, g, or t

<400> SEQUENCE: 16
ctctcatgtc ggccgttann nnnnnnnnnn nnnnnnnnnn nnnnnnnnnn nnnnnnnnta     60
acggccgaca tgagag                                                    76

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
taatacgact cactataggg acacaatgga cg                                   32

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
ctctcatgtc ggccgtta                                                   18

<210> SEQ ID NO 19
<211> LENGTH: 40
<212> TYPE: RNA
```

```
<213> ORGANISM: Artificial Sequence
<220> FEATURE:
<223> OTHER INFORMATION: Negative control RNA

<400> SEQUENCE: 19
gccauggugg ucaaccgucg guauugccgc aguuacuggc                           40

<210> SEQ ID NO 20
<211> LENGTH: 19
<212> TYPE: RNA
<213> ORGANISM: Artificial Sequence
<220> FEATURE:
<223> OTHER INFORMATION: Aptamer against midkine
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(19)
<223> OTHER INFORMATION: n is a, c, g, t or u

<400> SEQUENCE: 20
nnugnguggu uuauncgnn                                                  19

<210> SEQ ID NO 21
<211> LENGTH: 15
<212> TYPE: RNA
<213> ORGANISM: Artificial Sequence
<220> FEATURE:
<223> OTHER INFORMATION: Consensus sequence contained in aptamer against
      midkine

<400> SEQUENCE: 21
ugwgugguuu auccg                                                      15
```